United States Patent
Nahm et al.

(10) Patent No.: US 7,633,620 B2
(45) Date of Patent: Dec. 15, 2009

(54) LASER-INDUCED FLUORESCENCE DETECTION DEVICE AND METHOD

(75) Inventors: Kie-Bong Nahm, Seoul (KR); Eui-Yeol Choi, Gangwon-do (KR); Dong-Seok Jeong, Gangwon-do (KR); Jin-Ha Jung, Gangwon-do (KR); Joung-Dae Moon, Gyeonggi-do (KR); Young-Min Kim, Gangwon-do (KR); Keun-Woo Lee, Gangwon-do (KR); Jae-Soon Ahn, Gangwon-do (KR); Young-Eui Jeong, Gangwon-do (KR); Sang-Yeol Park, Gangwon-do (KR); Hyun-Mi Kim, Gangwon-do (KR); Byung-Ryong Lee, Gangwon-do (KR)

(73) Assignee: Boditechmed Inc., Chuncheon-si, Gangwon-do (KR)

( * ) Notice: Subject to any disclaimer, the term of this patent is extended or adjusted under 35 U.S.C. 154(b) by 0 days.

(21) Appl. No.: 12/327,942

(22) Filed: Dec. 4, 2008

(65) Prior Publication Data

US 2009/0114845 A1 May 7, 2009

Related U.S. Application Data

(62) Division of application No. 11/138,561, filed on May 26, 2005, now Pat. No. 7,476,549, and a division of application No. 10/502,378, filed on Jul. 23, 2004, now Pat. No. 7,371,582.

(30) Foreign Application Priority Data

| Jan. 23, 2002 | (KR) | ................. 10-2002-0003995 |
| Jan. 31, 2002 | (KR) | ................. 10-2002-0005755 |
| Jan. 23, 2003 | (WO) | ................. PCT/KR03/030015 |

(51) Int. Cl.
*G01N 21/25* (2006.01)

(52) U.S. Cl. .................................................. 356/417
(58) Field of Classification Search ......... 356/317–318, 356/417
See application file for complete search history.

(56) References Cited

U.S. PATENT DOCUMENTS 4,199,686 A * 4/1980 Brunsting et al. ........ 250/459.1

(Continued)

FOREIGN PATENT DOCUMENTS

| JP | 2227637 A | 9/1990 |
| JP | 11295311 | 10/1999 |
| KR | 1020020013172 A | 2/2002 |

OTHER PUBLICATIONS

Ye, Liwen, et al., "Competitive immunoassay for cyclosporine using capillary electrophoresis with laser induced fluorescence polarization detection," Journal of Chromotography B, 1998, pp. 59-67, vol. 714, Elsevier Science B.V.
Foreign communication from a related counterpart application —International Search Report, PCT/KR03/00151, May 9, 2003, 4 pgs.

*Primary Examiner*—Kara E Geisel
(74) *Attorney, Agent, or Firm*—Conley Rose, P.C.; J. Robert Brown, Jr.

(57) ABSTRACT

Disclosed is a lateral flow quantitative assay method which can measure one or more analyte species at the same time, with high sensitivity. Also, the present invention relates to a strip which can measure one or more analyte species at the same time, with high sensitivity and a package in which the strip is integrated with a laser-induced surface fluorescence detector. The present invention can quantify multiple analytes with a minimum detection limit of pg/ml. Therefore, the present invention provides an advantage capable of quantifying a plurality of analytes at the same time using a simple lateral flow assay strip.

1 Claim, 24 Drawing Sheets

U.S. PATENT DOCUMENTS

| | | | |
|---|---|---|---|
| 4,273,443 A * | 6/1981 | Hogg | 356/343 |
| 5,292,483 A * | 3/1994 | Kaye | 250/458.1 |
| 5,484,571 A * | 1/1996 | Pentoney et al. | 422/82.08 |
| 5,614,726 A | 3/1997 | Kaye et al. | |
| 5,998,146 A | 12/1999 | Latva et al. | |
| 6,136,549 A | 10/2000 | Feistel | |
| 6,316,274 B1 | 11/2001 | Herron et al. | |
| 6,340,598 B1 | 1/2002 | Herron et al. | |
| 6,451,619 B1 | 9/2002 | Catt et al. | |
| 7,371,582 B2 | 5/2008 | Nahm et al. | |
| 2001/0041339 A1 | 11/2001 | Anderson et al. | |
| 2002/0109841 A1* | 8/2002 | Gould et al. | 356/318 |
| 2005/0260666 A1 | 11/2005 | Nahm et al. | |

\* cited by examiner

LASER-INDUCED FLUORESCENCE DETECTION DEVICE AND METHOD

CROSS-REFERENCE TO RELATED APPLICATIONS

This is a Divisional Application which claims priority of U.S. Continuation-In-Part (C-I-P) application Ser. No. 11/138,561, filed May 26, 2005, entitled "Laser-induced Fluorescence Detection Device and Method" which claims priority of U.S. Pat. No. 7,371,582, issued May 13, 2008, entitled "Lateral Flow Quantitative Assay Method and Strip and Laser-induced Fluorescing Detection Device Therefor", which claims priority of Korean PCT application no. PCT/KR03/00151, entitled "Lateral Flow Quantitative Assay Method and Strip and Laser-Induced Fluorescing Detection Device Therefor", filed on 23 Jan. 2003 which claims priority of Korea patent application number 10-2002-0005755, filed Jan. 31, 2002, entitled "Lateral Flow Quantitative Assay Method and Strip and Laser-induced Fluorescence Detection Device Therefor"; and which claims priority of Korean patent application number 10-2002-0003995 entitled "Lateral Flow Quantitative Assay Method and Strip and Laser-induced Fluorescence Detection Device Therefor", filed on 23 Jan. 2002 all of which are hereby incorporated by reference for all purposes.

STATEMENT REGARDING FEDERALLY SPONSORED RESEARCH OR DEVELOPMENT

Not applicable.

REFERENCE TO A MICROFICHE APPENDIX

Not applicable.

The present invention relates to a lateral flow quantitative assay method which can measure one or more analyte species at the same time, with high sensitivity. Also, the present invention relates to a strip which can measure one or more analyte species at the same time, with high sensitivity and a package in which the strip is integrated with a laser-induced epifluorescence detector.

BACKGROUND OF THE INVENTION

Over the past 30 years, development of novel diagnostic apparatuses and methods which involve quantitative and qualitative analyses of extremely small quantities of substances contained in a sample taken for biopsy, such as blood or urine, has actively and rapidly progressed and even now, is still progressing at a high speed. RIA (Radioimmunological Assay) using radioactive isotopes was introduced in the 1950s, and ELISA (Enzyme Linked ImmunoSorbent Assay) was developed and advanced in the 1970s and 1980s. The ELISA method is the most popular laboratory test today and one of requisite tools for research in medical or life science fields. Recently, modified ELISA methods have been developed. Among them, for example, there is a method for analyzing a plurality of analytes at one time by immobilizing a plurality of antibodies onto a 96-well plate.

By typical immunodiagnostic methods, including RIA or ELISA, only one kind of analyte per sample can be quantified, using expensive analytical machinery and tools, while performing a multi-step procedure. Therefore, these methods cannot be readily used in a small-scale hospital, emergency room, the home, etc., where such equipments are not provided. In order to make up for this weak point, a convenient diagnostic kit using immunochromatography has been developed.

Using such diagnostic kit, it is possible to obtain a test result in 15 minutes after applying a sample such as whole blood, serum, urine, etc. to the kit. A representative type of immunochromatographic assays is a lateral flow assay. A kit for the lateral flow assay has a structure comprising a sample pad, to which a sample is applied, a releasing pad coated with a detector antibody, a developing membrane (typically, nitrocellulose) or strip, in which components of the sample move at different rates to be individually separated and to undergo antibody-antigen reaction, and an absorption pad which is provided at the far end of the sample pad to cause the sample to keep moving. The detector antibody is fixed onto, for example, colloidal gold particles to enable the detection. Latex beads or carbon particles may be used instead of gold particles. The diagnostic kit for the lateral flow assay is generally designed to detect an analyte in a sandwich configuration comprising the analyte, the detector antibody, and a capture antibody. Upon applying a liquid sample to the sample pad of the kit, an analyte contained in the sample begins to move from a sample pad. Firstly, the analyte reacts with a detector antibody releasably adhered to a releasing pad to form an antigen-antibody conjugate, which continues to develop in this conjugated form. Then, while moving through the developing membrane, the antigen-antibody conjugate reacts once more with a capture antibody fixed on a developing membrane to form a capture antibody-antigen-detector antibody conjugate in a sandwich form. Since the capture antibody is fixed on the developing membrane, conjugates are accumulated in the area where the capture antibodies are fixed. Proteins are invisible to the naked eye. Therefore, the presence and amount of conjugates are determined by means of an amount of gold particles attached to a certain area of the developing membrane.

The lateral flow assay can be widely and conveniently used in various fields such as pregnancy diagnosis, cancer diagnosis, and microbe detection. However, since quantification cannot be performed with the naked eye and hence, an exact amount of an analyte cannot be determined, its application is restricted. Especially, when a judgment should be made around a cut-off value, it is difficult to make an exact diagnosis. For example, in case of prostate cancer, when a detected value is 3.9 ng/ml which is very close to the standard cut-off value of 4 ng/ml, an exact diagnosis cannot be made.

Immunodiagnosis is now rapidly developing, and in the near future, will be able to easily and promptly identify and analyze a sample and diagnose disease conditions. The RIA or ELISA method which can quantify an analyte at present involves several complicated steps for such quantification, including treatment with an enzyme and washing. Similarly, the conventional convenient diagnostic kits have difficulties in providing quantified results. Therefore, there is a great demand for a general assay method which can perform quantification more rapidly, conveniently and sensitively. With the method, an ordinary unskilled person can practice diagnosis or analysis in any place.

The conventional lateral flow quantitative assay strips, including those disclosed in documents or products commercially available in the market, have a low sensitivity and are now used as means for performing a qualitative assay rather than a quantitative assay of analytes. Recently, in order to examine a disease state, several tens of analytes are generally analyzed, and numbers of analytes needed to be examined are tending to increase due to the rapid advance of molecular biology and medical science. However, at the present time, the individual analytes should be assayed separately, thereby increasing the burden of time and cost. Under the present circumstances, it would be advantageous in terms of economic aspects and other aspects to provide a method capable of rapidly and precisely quantifying different kinds of analytes at the same time, to satisfy demands of both general consumers and those involved in medical fields for development of such products.

SUMMARY OF THE INVENTION

The present inventors have developed a lateral flow quantitative assay method which is capable of quantifying a plurality of analytes at the same time with a minimum detection limit of pg/ml and a strip therefor, and a package comprising the strip and a laser-induced epifluorescence detector.

In accordance with an aspect, the present invention provides a lateral flow quantitative assay method in which a liquid sample which is expected to contain analytes is applied at one end of a chromatography medium to move through the chromatography medium, such that the analytes in the sample reacts with a labeled detector adsorbed on a section located at a predetermined distance from the sample application in the sample developing direction, thereby forming an analyte/labeled detector conjugate; in which the analyte/labeled detector conjugate, while moving through the chromatography medium, further reacts with an unlabeled captor which is different from or identical to the detector and is immobilized on a viewing window defined around middle portion of the chromatography medium, thereby forming a labeled detector/analyte/unlabeled captor conjugate in a sandwich configuration; and in which an amount of the conjugate is measured for quantitative determination of the analyte in the sample, characterized in that:

(a) the labeled detector is labeled with fluorescent material and reacts with the analytes in the liquid sample to form a fluorescently-labeled detector/analyte conjugate;

(b) the unlabeled captor is immobilized in lines within the viewing window on the chromatography medium and reacts with the fluorescently-labeled detector/analyte conjugate which has moved along the chromatography medium to form a fluorescently-labeled detector/analyte/unlabeled captor conjugate;

(c) a reference detector which is different from the detector and captor, is labeled with the same fluorescent material as the detector and reacts with reference material in the liquid sample, is adsorbed on the section of the chromatography medium where the fluorescently-labeled detector is adsorbed, and an unlabeled reference captor which reacts with the fluorescently-labeled reference detector is immobilized in a single reference line before or after the viewing window on the chromatography medium, or in double reference lines before and after the viewing window on the chromatography medium, whereby a reference conjugate of fluorescently-labeled reference detector/reference material/unlabeled reference captor is formed as the liquid sample passes through the chromatography medium; and (d) an amount of the analytes is determined by passing light emitted from a laser through an exciter filter, irradiating the filtered light to the epifluorescence medium containing the analyte conjugate and the reference conjugate, focusing light reflected from the epifluorescence medium to a first focal point of an elliptical or spherical reflecting mirror with a proper size, focusing scattered incident light and fluorescence emitted from the sample positioned at the first focal point of the elliptical reflecting mirror to a second focal point of the elliptical reflecting mirror, converting the focused light into parallel light by a collimator, filtering the parallel light through a fluorescent filter to remove the scattered incident light and provide a pure a fluorescence component to an optical detector, and comparing a fluorescence intensity of the analyte conjugate with a reference fluorescence intensity of the reference conjugate to determine the relative amount of the analyte.

In accordance with a second aspect, the present invention provides a lateral flow quantitative assay strip which comprises a backing, a sample pad adhered to one end of the backing and to which a liquid sample is applied, a conjugate releasing pad adhered to the backing such that one end of the sample pad overlaps with the end of the conjugate releasing pad closest to the end of the strip to which a sample is applied and upon which a labeled detector is releasably attached to react with an analyte in the liquid sample to form a conjugate, a chromatography medium adhered to the backing such that one end of the medium is overlapped by the end of the conjugate releasing pad farthest from the end of the strip to which the sample is applied and along which the sample develops and upon which a captor which is different from or identical to the detector and reacts with and traps the conjugate released from the conjugate releasing pad as the sample develops to form a sandwich type conjugate, and an absorption pad to absorb the sample developing along the chromatography medium and to absorb and remove unreacted labeled substances, characterized in that:

the detector releasably attached to the conjugate releasing pad is labeled with fluorescent material;

a reference detector which is labeled with the same fluorescent material as that of the detector and reacts with reference material in the liquid sample is further releasably attached to the conjugate releasing pad;

the labeled detector and the reference detector are present in a buffer solution not releasably attached to the pad, and the labeled detector reacts with the analyte in the liquid sample to form the detector-analyte conjugate labeled with fluorescence, in which the labeled detector reacts with the analyte to form a conjugate and the reference detector is different from the detector, the captor and the analyte;

the captor is immobilized in lines within a viewing window on the chromatography medium, an unlabeled reference captor which is different from the detector and captor is immobilized in a single reference line before or after the viewing window on the chromatography medium, or in double reference lines before and after the viewing window on the chromatography medium, whereby a conjugate of fluorescently-labeled detector/analyte/unlabeled captor and a reference conjugate of fluorescently-labeled reference detector/reference material/unlabeled reference captor are formed as the liquid sample passes through the chromatography medium; and an amount of the analytes is determined by passing light emitted from a laser through an exciter filter, irradiating the filtered light to the epifluorescence medium containing the analyte conjugate and the reference conjugate, focusing light reflected from the epifluorescence medium to a first focal point of an elliptical or spherical reflecting mirror, focusing scattered incident light and fluorescence emitted from the sample positioned at the first focal point of the elliptical reflecting mirror to a second focal point of the elliptical reflecting mirror, converting the focused light into parallel light by a collimator, filtering the parallel light through a fluorescent filter to remove the scattered incident light and provide a pure fluorescence component to an optical detector, and comparing a fluorescence intensity of the analyte conjugate with a reference fluorescence intensity of the reference conjugate to determine the relative amount of the analyte.

In accordance with a third aspect, the present invention provides a laser-induced epifluorescence detecting method which comprises steps of: passing light emitted from a laser through an exciter filter and focusing the filtered light to the surface of a sample positioned at a first focal point of an elliptical or spherical reflecting mirror with a proper size; focusing scattered incident light and fluorescence emitted from the sample positioned at the first focal point of the elliptical reflecting mirror to a second focal point of the elliptical reflecting mirror by reflection of the reflecting mirror; converting the focused light into parallel light by a collimator; filtering the parallel light through a fluorescent filter to remove the scattered incident light; and providing a pure a fluorescence component to an optical detector.

In accordance with a fourth aspect, the present invention provides a laser-induced epifluorescence detecting method which comprises steps of: passing light emitted from a laser through an exciter filter and focusing the filtered light to the surface of a sample positioned at a first focal point of an elliptical or spherical reflecting mirror with a proper size; focusing scattered incident light and fluorescence emitted from the sample positioned at the first focal point of the elliptical reflecting mirror to a spatial filter positioned at a second focal point of the elliptical reflecting mirror by reflection of the reflecting mirror; converting the filtered light into parallel light by a collimator; filtering the parallel light through a fluorescent filter to remove the scattered incident light; and providing a pure a fluorescence component to an optical detector.

In accordance with a fifth aspect, the present invention provides a laser-induced epifluorescence detecting apparatus comprising a laser, an exciter filter, an elliptical reflecting mirror or spherical mirror, epifluorescent sample control means, a collimator, a fluorescent filter and an optical detector, characterized in that the components of the detecting apparatus are arranged in a structure such that light emitted from a laser is passed through an exciter filter and is focused to the surface of a sample positioned at a first focal point of an elliptical reflecting mirror with a proper size, scattered incident light and fluorescence emitted from the sample positioned at the first focal point of the elliptical reflecting mirror are reflected from the elliptical reflecting mirror and focused upon a collimator as a second focal point of the elliptical reflecting mirror, by which the focused light is converted into parallel light and passed through a fluorescent filter to remove the scattered incident light, thereby providing a pure fluorescence component to an optical detector.

In accordance with a sixth aspect, the present invention provides a laser-induced epifluorescence detecting apparatus comprising a laser, an exciter filter, an elliptical reflecting mirror or spherical mirror, epifluorescent sample control means, a spatial filter, a collimator, a fluorescent filter and an optical detector, characterized in that the components of the detecting apparatus are arranged in a structure such that light emitted from a laser is passed through an exciter filter and is focused to the surface of a sample positioned at a first focal point of an elliptical reflecting mirror with a proper size, scattered incident light and fluorescence emitted from the sample positioned at the first focal point of the elliptical reflecting mirror are reflected from the elliptical reflecting mirror and focused to a spatial filter as a second focal point of the elliptical reflecting mirror, and filtered light is focused upon a collimator, by which the focused light is converted into parallel light and passed through a fluorescent filter to remove the scattered incident light, thereby providing a pure fluorescence component to an optical detector.

In accordance with a seventh aspect, the present invention provides a package for quantitative assay comprising (i) a lateral flow quantitative assay strip comprising a backing, a sample pad adhered to one end of the backing and to which a liquid sample is applied, a conjugate releasing pad adhered to the backing such that one end of the sample pad overlaps with the end of the conjugate releasing pad closest to the end of the strip to which the sample is applied and upon which a labeled detector is releasably attached to react with an analyte in the liquid sample to form a conjugate, a chromatography medium adhered to the backing such that one end of the medium is overlapped by the end of the conjugate releasing pad farthest from the end of the strip to which the sample is applied and along which the sample develops and upon which a captor which is different from or identical to the detector and reacts with and traps the conjugate released from the conjugate releasing pad as the sample develops to form a sandwich type conjugate, and an absorption pad to absorb the sample developing along the chromatography medium and to absorb and remove unreacted labeled substances; in which the detector releasably attached to the conjugate releasing pad is labeled with fluorescent material, a reference detector which is labeled with the same fluorescent material as that of the detector and reacts with reference material in the liquid sample is further releasably attached to the conjugate releasing pad, the captor is immobilized in a line within a viewing window on the chromatography medium, an unlabeled reference captor which is different from the detector and captor is immobilized in a single reference line before or after the viewing window on the chromatography medium, or in double reference lines before and after the viewing window on the chromatography medium, and (ii) a laser-induced epifluorescence detecting apparatus comprising a laser, an exciter filter, an elliptical reflecting mirror or spherical mirror, epifluorescence sample control means, a collimator, a fluorescent filter and an optical detector, characterized in that:

the components of the detecting apparatus are arranged in a structure such that light emitted from a laser is passed through an exciter filter and irradiated to the epifluorescence medium containing the analyte conjugate of fluorescently-labeled detector/analyte/unlabeled captor formed in the viewing window and the reference conjugate of fluorescently-labeled reference detector/reference material/unlabeled reference captor formed in the reference lines as the liquid sample passes through the chromatography medium of the strip, light reflected from the surface is focused to a first focal point of an elliptical or spherical reflecting mirror with a proper size, scattered incident light and fluorescence emitted from the sample positioned at the first focal point of the elliptical reflecting mirror are reflected from the elliptical reflecting mirror and focused to a collimator as a second focal point of the elliptical reflecting mirror, by which the focused light is converted into parallel light and passed through a fluorescent filter to remove the scattered incident light, thereby providing a pure fluorescence component to an optical detector, in which a fluorescence intensity of the conjugate and a reference fluorescence intensity of the reference conjugate, each being formed on the strip, are measured, and which is capable of determining the quantity of the analyte in the liquid sample by comparing the fluorescence intensities of the conjugates measured by the laser-induced epifluorescence detecting apparatus.

DETAILED DESCRIPTION OF THE PREFERRED EMBODIMENTS

Figure 1:
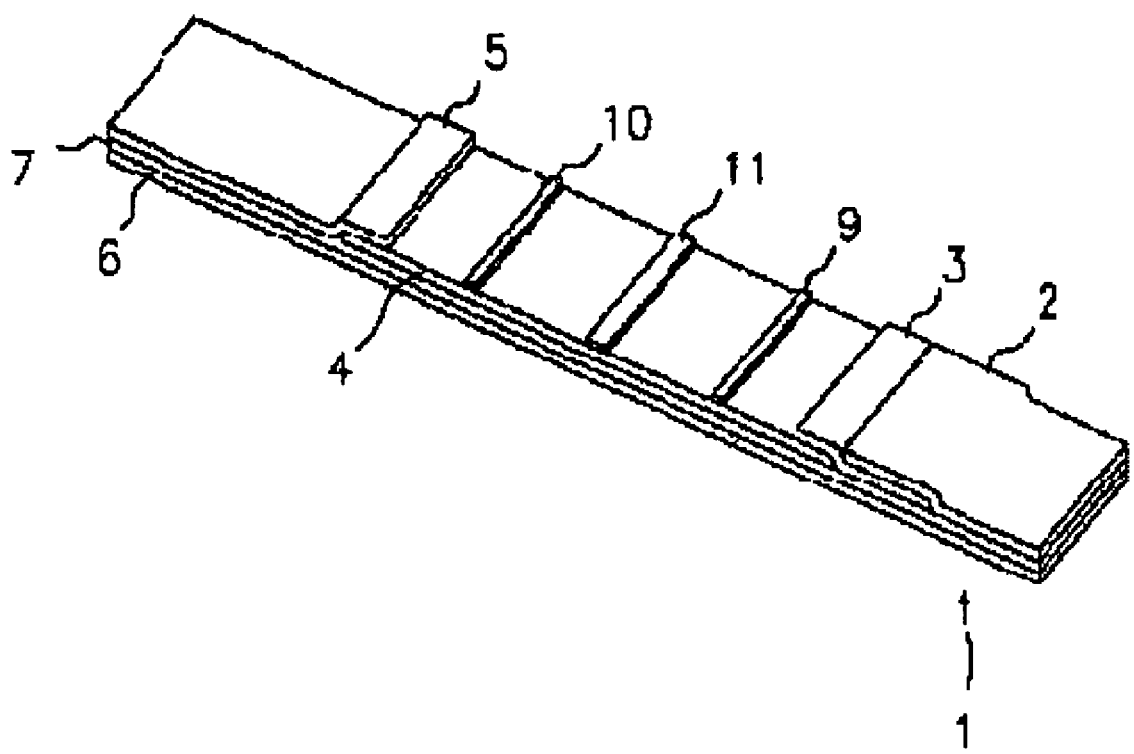
FIG. 1 is a perspective view of the conventional lateral flow quantitative assay strip.

The term "sensitivity" as used herein refers to a minimum quantity of a conjugate of a captor, detector and analyte which can be detected.

The term "epifluorescence" as used herein refers to the fluorescence emitted from a conjugate of fluorescently-labeled detector/analyte/captor and/or a reference conjugate of fluorescently-labeled reference detector/reference material/reference captor, which are fixed in a viewing window and a reference line, respectively, of the lateral flow assay strip by chromatography.

The term "analyte" as used here in refers to a compound or composition being analyzed in a liquid sample. The samples which are usable in the present invention may be selected from any samples containing such an analyte. Examples include physiological fluid such as urine, serum, plasma, blood, saliva, spinal fluid, ocular liquid, amniotic fluid, etc., food such as milk and wine, chemical treatment stream such as domestic waste water. Analytes that can be examined in the present invention are largely classified into a complete antigen and a hapten (incomplete antigen). The complete antigen refers to an antigenic substance which itself has the ability to induce antibody production (immunogenicity), and mainly includes peptide hormones having high molecular weights. The hapten (incomplete antigen) refers a material which can bind to an antibody but has no ability to induce antibody production by itself, and includes peptides having relatively low molecular weights (molecular weights of about 1,000 or less). Haptens acquire the ability to induce antibody production when bound to a protein such as bovine serum albumin.

For the purposes of the present invention, examples of the complete antigens are described below, but are not limited thereto:

(1) Examples of peptide hormones
   1) Pituitary hormones such as growth hormone (GH), adrenocorticotropic hormone (ACTH), melanocyte-stimulating hormone (MSH), prolactin, thyroid-stimulating hormone (TSH), luteinizing hormone (LH), follicle-stimulating hormone (FSH) and oxytocin;
   2) Calcium metabolic regulatory hormones such as calcitonin and parathyroid hormone;
   3) Insulin, proinsulin and pancreatic hormone;
   4) Alimentary canal hormones such as gastrin and secretin;

5) Hormones which act on blood vessels such as angiotensin and bradykinin; and
6) Placental hormones such as human chorionic gonadotropin (hCG) and human placental lactogen (hPL).

(2) Examples of other substances
1) Enzymes such as prostatic acidic phosphatase (PAP), prostate-specific antigen (PSA), alkaline phosphatase, transaminase, lactic acid dehydrogenase (LDH), transaminase, trypsin and pepsinogen;
2) Cancer-specific substances such as α-fetoprotein (AFP) and cancer embryonic antigen (CEA);
3) Serum protein components such as immunoglobulin G (IgG), fibrin-fibrinogen decomposition products (FDP, D-dimer), antithrombin III (ATIII) and transferrin; and
4) Substances such as rheumatoid factor, serotonin, urokinase, ferritin and substance P.

For the purposes of the present invention, examples of haptens are described below, but are not limited thereto:
(1) Steroidal haptens
1) Estrogens such as estrone, estradiol, estriol, estetrol, equilin and equilenin;
2) Natural or synthetic luteohormones such as progesterone, pregnanediol, pregnanetriol, 19-norethisterone and chloromadinone acetate;
3) Male sex hormones such as testosterone, dehydroepiandrosterone, dihydrotestosterone, androsterone and etiocholanorone;
4) Adrenal cortical hormones such as cortisol, cortisone, deoxycorticosterone, aldosterone and tetrahydrocortisol; and
5) Bile acids such as vitamins D, cholesterol, cholic acid, deoxycholic acid and chenocholic acid, and other steroids such as cardiotonic steroid, saponin and sapogenin.

(2) Physiologically active amines
1) Catecholamines such as epinephrine, norepinephrine, dopamine and ephedrine, and metabolites thereof;
2) Physiologically active alkaloids such as morphine, codeine, heroin, morphine chloride, cocaine, mescaline, papaverine, narcotine, yohimbine, reserpine, ergotamine and strychnine; and
3) Amino group-containing psychotropics such as LSD, amphetamine, methamphetamine and meprobamate.

(3) Other examples
1) Low-molecular-weight peptides having no antigenicity such as TRH and LH-RH;
2) Thyroid hormones such as diiodothyronine, triiodothyronine and thyroxine;
3) Prostaglandins such as prostaglandin E2, prostaglandin E3 and prostaglandin F1α;
4) Vitamins such as vitamin A, B vitamins (vitamins B1, B2, B6 and B12, and the like), vitamin E and vitamin K;
5) Antibiotics such as penicillin, actinomycin, chloromycetin and tetracycline; and
6) Other in vivo components, and drugs administered into organisms and metabolites thereof.

According to the present invention, the analytes are characterized by being monoepitopic or polyepitopic. The polyepitopic ligand analytes will normally be poly(amino acids) i.e. polypeptides and proteins, polysaccharides, nucleic acids, and combinations thereof. Such combinations of assemblages include bacteria, viruses, chromosomes, genes, mitochondria, nuclei, cell membranes, and the like. For the most part, the polyepitopic ligand analytes employed in the present invention will have a molecular weight of at least about 5,000, more usually at least about 10,000. In the poly(amino acid) category, the poly(amino acids) of interest will generally be from about 5,000 to 5,000,000 in molecular weight, more usually from about 20,000 to 1,000,000 in molecular weight, and among the hormones of interest, the molecular weights will usually range from about 5,000 to 60,000.

The wide variety of proteins may be classified into families of proteins having similar structural features, proteins having particular biological functions, proteins related to specific microorganisms, particularly disease causing microorganisms, etc. For cells and viruses, histocompatability antigens or surface antigens will frequently be of interest.

The proteins related by structure are classified into protamines, histones, albumins, globulins, scleroproteins, phosphoproteins, mucoproteins, chromoproteins, lipoproteins, nucleoproteins, glycoproteins, and proteoglycans. In addition, unclassified proteins, for example, somatotropin, prolactin, insulin, pepsin and the like may be included. All of these proteins can be quantified by the package comprising the lateral flow assay strip and the laser-induced epifluorescence detecting apparatus according to the present invention.

A number of proteins found in human plasma which are clinically important can also be quantified by the package comprising the lateral flow assay strip and the laser-induced epifluorescence detecting apparatus according to the present invention, Examples of such plasma proteins include prealbumin, albumin, $\alpha_1$-lipoprotein, $\alpha_1$-acid glycoprotein, $\alpha_1$-antitrypsin, $\alpha_1$-glycoprotein, transcortin, 4.6S-postalbumin, tryptophan-poor $\alpha_1$-glycoprotein, $\alpha_1$X-glycoprotein, thyroxin-binding globulin, inter-α-trypsin-inhibitor, Gc-globulin (Gc 1-1, Gc 2-1 and Gc 2-2), haptoglobin (Hp 1-1, Hp 2-1 and Hp 2-2), ceruloplasmin, cholinesterase, $\alpha_2$-lipoprotein(s), myoglobin, C-reactive protein, $\alpha_2$-macroglobulin, $\alpha_2$-HS-glycoprotein, Zn-$\alpha_2$-glycoprotein, $\alpha_2$-neuramino-glycoprotein, erythropoietin, β-lipoprotein, transferrin, hemopexin, fibrinogen, plasminogen, $\beta_2$-glycoprotein I, $\beta_2$-glycoprotein II, immunoglobulin G (IgG), A (IgA), M (IgM), D (IgD), E (IgE) and the like.

Other examples of analytes which can be quantified by the package comprising the lateral flow assay strip and the laser-induced epifluorescence detecting apparatus according to the present invention are complement factors and blood clotting factors. Examples of the complement factors include C'1, C'1q, C'1r, C'1s, C'2, C'3 ($\beta_1$A and $\alpha_2$D), C'4, C'5, C'6, C'7, C'8 and C'9. Important blood clotting factors include fibrinogen, prothrombin, thrombin, tissue thromboplastin, proaccelerin, globulin (accelerator of proaccelerin), proconvertin, antihemophilic globulin (AHG), Christmas factor (plasma thromboplastin component (PTC)), Stuart-Prower factor (autoprothrombin III), plasma thromboplastin antecedent (PTA), Hagemann factor and fibrin-stabilizing factor.

Important protein hormones which can be quantified by the package according to the present invention include, but are not limited to, peptide and protein hormones such as parathyroid hormone (parathromone), thyrocalcitonin, insulin, glucagons, relaxin, erythropoietin, melanotropin, somatotropin (growth hormone), corticotropin, thyrotropin, follicle-stimulating hormone, luteinizing hormone, luteomammotropic hormone and gonadotropin (chorionic gonadotropin); tissue hormones such as secretin, gastrin, angiotensin I and II, bradykinin and human placental lactogen; peptide hormones from the neurohypophysis such as oxytocin, vasopressin, and releasing factors (RF)(CRF, LRF, TRF, somatotropin-RF, GRF, FSH-RF, PIF, MIF).

Still other analytes which can be quantified by the package according to the present invention include antigenic polysaccharides derived from microorganisms. Examples of the antigenic polysaccharides derived from microorganisms include, but are not limited to hemosensitins found in *Streptococcus pyogenes* polysaccharide, *Diplococcus pneumoniae* polysaccharide, *Neisseria meningitidis* polysaccharide, *Neisseria gonorrhea* polysaccharide, *Corynebacterium diphtheriae* polysaccharide, *Actinobacillus mallei* crude extract, *Francisella tularensis* lipopolysaccharide and polysaccharide, *Pasteurella pestis* polysaccharide, *Pasteurella* multocida capsular antigen, *Brucella abortus* crude extract, *Haemophilus influenzae* polysaccharide, *Haemophilus pertussis* crude extract, *Treponema reiteri* polysaccharide, *Veillonella* lipopolysaccharide, *Erysipelothrix* polysaccharide, *Listeria monocytogenes* polysaccharide, *Chromobacterium* lipopolysaccharide, *Mycobacterium tuberculosis* aline extract of 90% phenol-extracted mycobacteria and polysaccharide fraction, *Klebsiella aerogenes* polysaccharide, *Klebsiella cloacae* polysaccharide, *Salmonella typhosa* liposaccharide and polysaccharide, *Salmonella typhimurium* polysaccharide, *Shigella dysenteriae* polysaccharide, *Shigella flexneri* and *Shigella sonnei* crude extract and polysaccharide, *Rickettsiae* crude extract, *Candida albicans* polysaccharide and *Entamoeba histolytica* crude extract.

The microorganisms which are assayed using the package according to the present invention may be intact, lysed, ground or otherwise fragmented. Examples of such microorganisms include *Corynebacteria, Corynebacterium diptheriae, Pneumococci, Diplococcus pneumoniae, Streptococci, Streptococcus pyogenes, Streptococcus salivarus, Staphylococci, Staphylococcus aureus, Staphylococcus albus, Neisseriae, Neisseria meningitides, Neisseria gonorrheae, Enterobacteriaciae, Escherichia coli, Aerobacter aerogenes, Klebsiella pneumoniae bacteriam, Salmonella typhosa, Salmonella choleraesuis, Salmonella typhimurium, Shigella dysenteriae, Shigella schmitzii, Shigella arabinotarda, Shigella flexneri, Shigella boydii, Shigella Sonnei, Proteus vulgaris, Proteus mirabilis, Proteus morgani, Pseudomonas aeruginosa, Alcaligenes faecalis, Vibrio cholerae, Hemophilus influenzae, Hemophilus ducreyi, Hemophilus hemophilus, Hemophilus aegypticus, Hemophilus parainfluenzae, Bordetella pertussis, Pasteurellae, Pasteurella pestis, Pasteurella tulareusis, Brucellae, Brucella melitensis, Brucella abortus, Brucella suis, Bacillus anthracis, Bacillus subtilis, Bacillus megaterium, Bacillus cereus, Clostridium tetani, Clostridium perfringens, Clostridium novyi, Clostridium septicum, Clostridium histolyticum, Clostridium tertium, Clostridium bifermentans, Clostridium sporogenes, Mycobacteria, Mycobacterium tuberculosis hominis, Mycobacterium bovis, Mycobacterium avium, Mycobacterium leprae, Mycobacterium paratuberculosis, Actinomyces israelii, Actinomyces bovis, Actinomyces naeslundii, Nocardia asteroids, Nocardia brasiliensis, Spirochetes, Treponema pallidum Spirillum minus, Treponema pertenue Streptobacillus, Treponema carateum, Borrelia recurrentis, Leptospira icterohemorrhagiae, Leptospira canicola, Mycoplasmas, Mycoplasma pneumoniae, Listeria monocytogenes, Erysipelothrix rhusiopathiae, Streptobacillus moniliformis, Donvania granulomatis, Bartonella bacilliformis, Rickettsia prowazekii, Rickettsia mooseri, Rickettsia rickettsii, Rickettsia conori, Rickettsia australis, Rickettsia sibiricus, Rickettsia akari, Rickettsia tsutsugamushi, Rickettsia burnetii, Rickettsia Quintana, Chlamydia, Cryptococcus neoformans, Blastomyces dermatidis, Histoplasma capsulatum, Coccidioides immitis, Paracoccidioides brasiliensis, Candida albicans, Aspergillus fumigatus, Mucor corymbifer (Absidia corymbifera), Rhizopus oryzae, Rhizopus arrhizus, Rhizopus nigricans, Sporotrichum schenkii, Fonsecaea pedrosoi, Fonsecaea compacta, Fonsecae dermatidis, Cladosporium carrionii, Phialophora verrucosa, Aspergillus nidulans, Madurella mycetomi, Madurella grisea, Allescheria boydii, Phialosphora jeansilmei, Microsporum gypseum, Trichophyton mentagrophytes, Keratinomyces ajelloi, Microsporum canis, Trichophyton rubrum, Microsporum adnouini,* Adenoviruses, Herpes Viruses, Herpes simplex, *Varicella,* Herpes Zoster, Cytomegalovirus, Pox Viruses, Variola, Vaccinia, Poxvirus bovis, Paravaccinia, *Molluscum contagiosum*, Picaornaviruses, Poliovirus, Coxsackievirus, Echoviruses, Rhinoviruses, Myxoviruses, Influenza (A, B, and C), Parainfluenza (14), Mumps Virus, Newcastle Disease Virus, Measles Virus, Rinderpest Virus, Canine Distemper Virus, Respiratory Syncytial Virus, Rubella Virus, Arboviruses, Eastern Equine Eucephalitis Virus, Western Equine Eucephalitis virus, Sindbis Virus, Chikugunya Virus, Semliki Forest Virus, Mayora Virus, St. Louis Encephalitis Virus, California Encephalitis Virus, Colorado Tick Fever Virus, Yellow Fever Virus, Dengue Virus, Reovirus Types 1-3, Hepatitis A Virus, Hepatitis B Virus, Tumor Viruses, Rauscher Leukemia Virus, Gross Virus, Maloney Leukemia Virus, Epstein Barr Virus, and other parasites related to diseases such as Dog Heart Worm (microfilaria), Malaria, Schistosomiasis, Coccidosis and Trichinosis.

The monoepitopic ligand analytes which can be quantified using the package of the present invention will generally have a molecular weight from about 100 to 2,000, more usually from 125 to 1,000. Representative examples of the analytes include drugs, metabolites, pesticides, pollutants, and the like. Included among drugs are the alkaloids. Among the alkaloids are morphine alkaloids, for example morphine, codeine, heroin, dextromethorphan, their derivatives and metabolites; cocaine alkaloids, for example cocaine and benzoyl ecgonine, their derivatives and metabolites; ergot alkaloids, for example the diethylamide of lysergic acid; steroid alkaloids; iminazoyl alkaloids; quinazoline alkaloids, insoquinoline alkaloids; quinoline alkaloids, for example quinine and quinidine; diterpene alkaloids; and their derivatives and metabolites.

Also, drugs of steroids can be quantified by the package of the present invention. Specific examples thereof include estrogens, gestogens, androgens, andrenocortical steroids, bile acids, cardiotonic glycosides and aglycones, for example digoxin and digoxigenin, saponins and sapogenins, their derivatives and metabolites. Further included are the steroid mimetic substances, such as diethylstilbestrol. Another group of drugs which can be quantified by the package of the present invention is lactams having from 5 to 6 annular members, which include the barbiturates, for example, phenobarbital and secobarbital, diphenylhydantonin, primidone, ethosuximide, and metabolites thereof. The next group of drugs is aminoalkylbenzenes, in which the alkyl group has from 2 to 3 carbon atoms. Examples include the amphetamines, catecholamines such as ephedrine, L-dopa, epinephrine, narceine, papaverine, and metabolites thereof. The next group of drugs is benzheterocyclics, for example oxazepam, chlorpromazine, tegretol, imipramine, and derivatives and metabolites thereof, in which the heterocyclic rings are azepines, diazepines and phenothiazines. The next group of drugs is purines, for example theophylline, caffeine, and metabolites and derivatives thereof. The next group of drugs includes those derived from marijuana, for example cannabinol and tetrahydrocannabinol. The next group of drugs includes the vitamins such as A, B, for example $B_{12}$, C, D, E and K, folic acid, and thiamine. The next group of drugs is prostaglandins, which differ by the degree and sites of hydroxylation and unsaturation. The next group of drugs is antibiotics, for example, penicillin, chloromycetin, actinomycetin, tetracycline, terramycin, and metabolites and derivatives thereof. The next group of drugs is the nucleosides and nucleotides, for example, ATP, NAD, FMN, adenosine, guanosine, thymidine, and cytidine with their appropriate sugar and phosphate substituents. The next group of drugs is miscellaneous individual drugs, for example, methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, and metabolites and derivatives thereof. Metabolites related to conditions of disease include spermine, galactose, phenylpyruvic acid and porphyrin Type 1. The next group of drugs is aminoglycosides, such as gentamicin, kanamycin, tobramycin, and amikacin.

The analytes which can be quantified by the package of the present invention also include pesticides. Their examples are polyhalogenated biphenyls, phosphate esters, thiophosphates, carbamates, polyhalogenated sulfenamides, metabolites and derivatives thereof.

The analytes which can be quantified by the package of the present invention further include receptor analytes, whose molecular weights will generally range from 10,000 to $2\times10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 6,000,000 in molecular weight. Natural receptors vary widely, generally being at least about 25,000 molecular weight and may have a molecular weight of 106 or higher, including such materials as avidin, thyroxine binding globulin, thyroxine binding prealbumin, transcortin, etc.

In addition to the above-described analytes, the package of the present invention may be used to quantify tumor markers, angiogenesis related markers, cardiac markers, Alzheimer disease related markers, cancer related genes, environmental toxins, abused drugs and the like. As examples of the tumor markers, alpha 1-acidglycoprotein, CEA, AFP, PSA/free PSA, CA 15-3, CA 19-9, CA 27-9, CA-50, CA 125, CA 72-4, calcitonin, elastase-1, ferritin, pepsinogen 1, PIVKA II, Procollagen III peptide, beta HCG, beta 2-microglobulin, neuron specific enolase, CYFRA 21-1 (Cytokeratin 19), Secretin, NMP (nuclear matrix protein), COX-1, TPA (Tissue Polypeptide, Antigen) and the like may be included. The angiogenesis related markers include angiogenic factors and angiostatic factors. Specific examples of the angiogenic factors include aFGF (acidic Fibroblast Growth Factor), bFGF (basic Fibroblast Growth Factor), VEGF (Vascular Endothelial Growth Factor), angiogenin, angiopoietin 1, heparinase, scatter factor, HGF (Hepatocyte Growth Factor), PDGF (Platelet Derived Growth Factor), Pleiotrophin, TGF α, TFG β, IL-8, TNF α, and prostagladins E1 and E2. Specific examples of the angiostatic factors include endostatin, angiostatin, cartilage-derived inhibitor, heparinase, angiopoietin2, IFN α, IFN β, IFN γplatelet factor 4, 16 kDa prolactin fragment, protamine, thrombospandin, TIMPs (Tissue Inhibitor of Metalloproteinase), thalidomide and TNP 470 (Fumagilin analogue). Examples of the cardiac markers include creatin kinase-BB, creatin kinase-MB, creatin kinase-MM, myoglobin, MLC (Myosin Light Chain), troponin I, troponin C, troponin ITC, troponin T, CRP and FABP (Fatty Acid Binding Protein). Examples of the Alzheimer disease related markers include glutamine synthetase, melano transferrin and β-amyloid protein. Examples of the cancer related gene include bcl-2, C-erbB-2, C-myc, CSF-1 receptor, EGF receptor, H-ras, K-ras (p12), L-myc, mdr-1, N-myc, N-ras, p53 exon 4, p53 exon 5, p53 exon 6, p53 exon 7, p53 exon 8, p53 exon 9, TcR-α, TCR-β, TcR-γ and TcR-δ. The environmental toxins include for example, microcystin, dioxin and PCB. Examples of the abused drugs include amphetamines, barbiturates, benzodiazepin, cannabinoids, cocaine, morphine, phencyclidine and TBPE.

According to the present invention, as a label which can act as an indicator of presence or absence of an analyte in a liquid sample, fluorescent material is specifically used. The useful fluorescent material may have a difference of 20 nm or more between its absorption wavelength and emission wavelength. Representative examples of the fluorescent material include, but are not limited to, fluorescent particles, quantum dots, lanthanide chelates, such as samarium (Sm), Europium (Eu) and Terbium (Tb), and fluors, such as FITC, Rhodamine green, thiadicarbocyanine, Cy2, Cy3, Cy5, Cy5.5, Alexa 488, Alexa 546, Alexa 594 and Alexa 647). Preferred fluorescent materials which can be used in detection of DNA are Cy3 and Cy5. In general, the fluorescence intensity is directly proportional to the intensity of excitation light.

According to the present invention, the labeling material binds to the detector which specifically binds to an analyte via a linker. Such linkers include, but are not limited to, N-[k-Maleimidoundecanoyloxy])-sulfosuccinimide ester (sulfo-KMUS), succinimidyl-4-(N-maleimidomethyl)cyclohexane-1-carboxy[6-Amidocaproate] (LC-SMCC), K,K-maleimidoundecanoic acid (KMUA), succinimidyl-4-[p-maleimidophenyl]butyrate (SMBP), succinimidyl-6-[(β-maleimido-propionamido)hexanoate (SMPH), Succinimidyl-(N-maleimidomethyl)cyclohexane-1-carboxylate (SMCC), sulfosuccinimidyl-4-(N-maleimidomethyl)cyclohexane-1-carboxylate (sulfo-SMCC), N-succinimidyl (4-iodoacetyl) aminobenzoate (SIAB), sulfosuccinimidyl-(4-iodoacetyl)aminobenzoate (sulfo-siab), N-[γ-maleimidobutyryloxy]-sulfo-succininimide ester (sulfo-GMBS), N-[γ-maleimidobutyryloxy]-succininimide ester (GMBS), succinimidyl 3-(bromoacetamido) propionate (SBAP), N-β-maleimidopropionic acid (BMPA), N-[α-maleimidoacetoxy]succinimide ester (AMAS), N-succinimidyl S-acetylthiopropionate (SATP), m-maleimidobenzoyl-N-hydroxysuccinimide ester (MBS), m-maleimidobenzoyl-N-hydroxysulfosuccinimide ester (sulfo-MBS), N-e-maleimidocapric acid (EMCA), N-[e-maleimidocaproyloxy] succinimide ester (EMCS), N-succinimidyl-[4-vinylsulfonyl]benzoate (SVSB), N-[β-maleimidopropyloxy] succinimide ester (BMPS) and 1-ethyl-3-[3-dimethylaminopropyl]carbodiimide hydrochloride (EDC). These linkers will react with thiol groups of the detector.

The lateral flow assay strip of the present invention may take a shape of a rectangle, circle, oval, triangle and other various shapes, provided that there should be at least one direction along which a test solution moves by capillarity. In case of an oval or circular shape, in which the test solution is initially applied to the center thereof, there are different flow directions. However, what is taken into consideration is that the test solution should move in at least one direction toward a predetermined position. Thickness of the strip according to the present invention is usually 0.1 to 2 mm, more usually 0.15 to 1 mm, preferably 0.2 to 0.7 mm, though it is not important. In general, a minimum thickness is determined depending on a strength of the strip material and needs for producing a readily detectable signal while, a maximum thickness is determined depending on handling ease and cost of reagents. In order to maintain reagents and provide a sample of a defined size, the strip is constructed to have a relatively narrow width, usually less than 20 mm, preferably less than 10 mm. In general, the width of the strip should be at least about 1.0 mm, typically in a range of about 2 mm to 12 mm, preferably in a range of about 4 mm to 8 mm. The length of the strip is determined considering kinds of analytes, the number of test lines or spots and the number of reference lines on the chromatography medium, space between pads, convenience of handling and the like. Usually, it is 1 to 40 cm, preferably about 2 to 25 cm, more preferably about 4 to 20 cm. However, the strip can be practically prepared to have any length.

Solvents for a liquid sample to be analyzed are commonly aqueous media, which include oxidizing solvents having usually 1 to 6 carbon atoms, more usually 1 to 4 carbon atoms containing about 40 wt % or less of another polar solvent, particularly alcohol, ether, etc. In common, a cosolvent is contained in an amount of less than about 20 wt %. Under some circumstances according to the nature of an analyte, a part or all of the aqueous medium can be provided by the analyte per se.

The aqueous medium has pH of typically 4 to 11, more typically 5 to 10, preferably 6 to 9. The pH is selected in accordance with critical binding affinity sites of the binding elements and ability to maintain voluntary generation of signals by a signal generation system. Various buffers can be used to adjust pH to a desired level and maintain pH at that level during an assay. Representative buffers include for example, borate, phosphate, carbonate, Tris, and barbital. Though usable buffers are not particularly important, a certain buffer can be preferred for individual assays as opposed to other buffers. Also, a non-ionic detergent can be preferably added to the sample in an amount of about 0.05 to 0.5 wt %. In addition, a variety of polyoxyalkylene compounds of about 200 to 20,000 Daltons can be used.

Typically, the assay is carried out at a mild temperature and preferably, is carried out at a substantially constant temperature. A suitable temperature for generating assay signal is usually about 4° C. to 50° C., more usually about 10° C. to 40° C., frequently ambient temperature, i.e. about 15° C. to 25° C.

The concentration of the analyte to be analyzed in a subject solution is typically about $10^4$ to about $10^{-15}$ M, more typically about $10^{-6}$ to $10^{-14}$ M. The concentrations of other reagents is commonly determined considering the concentration of a desired analyte and protocol.

In general, concentrations of various reagents in a sample and reagent solution are determined in accordance with a concentration range of a target analyte and a final concentration of each reagent is determined empirically to optimize the sensitivity of the assay within a target range. Each reagent can be used in an excess amount along with a certain protocol, as long as it does not lower the sensitivity of the assay.

Now, the package integratedly formed of the lateral flow assay strip and the laser-induced epifluorescence detecting apparatus will be explained in detail.

Backing of the Lateral Flow Assay Strip

The backing is typically made of water-insoluble, non-porous and rigid material and has a length and width equal to the pads situated thereon, along which the sample develops, but may have a dimension being less or greater than the pad. In preparation of the backing, various natural and synthetic organic and inorganic materials can be used, provided that the backing prepared from the material should not hinder capillary actions of the absorption material, nor non-specifically bind to an analyte, nor interfere with the reaction of the analyte with a detector. Representative examples of polymers usable in the present invention include, but are not limited to, polyethylene, polyester, polypropylene, poly(4-methyl-butene), polystyrene, polymethacrylate, poly(ethylene terephthalate), nylon, poly(vinyl butyrate), glass, ceramic, metal and the like.

On the backing, a variety of pads are adhered by means of adhesives. Proper selection of adhesives may improve the performance of the strip and lengthen the shelf life of the strip. According to the present invention, pressure-sensitive adhesives (PSA) may be representatively used in the lateral flow assay strip. Typically, the adhesion of different pads of the lateral flow assay strip is accomplished as the adhesive penetrates into pores of the pads, thereby binding pads together with the backing. With respect to such binding, ability of an adhesive to flow under normal conditions is referred to as "cold flow". Since no heat is applied when coating PSA on to the pad, cold flow of a certain level is indispensable for binding between the pad and the backing. If the level of cold flow is too low, the initial binding force is low, causing insufficient binding between the pad and the backing. In contrast, if the level of cold flow is too high, the adhesive migrates to the pads with which it is bound during storage of the strip, thereby clogging the pores, forming hydrophobic stains or leading to problems of redamping the pad. Such problems associated with the cold flow of the adhesive can be solved by using a direct-casting membrane. For example, in the direct-casting membrane, a supporting plastic sheet prevents the adhesive from entering pores of the membrane and thus vertical migration of the adhesive is prevented during storage.

Sample Pad of the Lateral Flow Assay Strip

The sample pad basically acts to receive the fluid sample containing an analyte. Other than this function, the sample pad may have a function to filter insoluble particles in the sample. From this point of view, preferred sample pads of the present invention are composed of cellulose filter paper or glass fiber filter paper capable of providing the filtering function. Usually, a cellulose membrane (grade 903) produced by S & S is used.

Preferably, the sample pad is treated in advance to prevent the analyte in the sample from being non-specifically adsorbed thereto, to allow the components of the sample to readily migrate through the chromatography medium, to maintain the sensitivity of the reaction and to prevent undesirable nonspecific reactions which may occur between the labeled detector and components of the sample. The pretreatment of the sample pad is generally performed by treating the pad with an inactive protein or surfactant. For instance, the pretreatment is carried out by immersing the pad material in a solution of 0.1 to 10% bovine serum albumin (BSA)-containing 0.1 M Tris buffer solution (pH 6-9), a solution of 0.1% to 10% skim milk powder in 0.1 M Tris buffer solution (pH 6-9) and/or 0.1 to 10% casein solution. After leaving the sample pad as it is at 37° C. for 1 hour or at 4° C. for 1 day, the sample pad is removed from the solution and washed with a Tris buffer solution and dried. The pretreatment with a surfactant is carried out by immersing the pad in for example, 0.01% to 1% solution of Triton X-100 or Tween 20, non-ionic surfactant, followed by drying. Preferably, the sample pad may be treated with an inactive protein and then a surfactant. However, these pretreatment steps are determined in accordance with kinds of analytes and samples.

Conjugate Releasing Pad of the Lateral Flow Assay Strip

On the conjugate releasing pad of the lateral flow assay strip according to the present invention, a fluorescently-labeled detector capable of reacting with an analyte in the sample to form a conjugate is adhered but is not immobilized. Since the detector is releasably attached, when forming a conjugate via reaction with an analyte in the sample, it can move together with the sample through the chromatography medium.

It is preferred for material of the conjugate releasing pad to have a rapid filtering speed and a good ability to hold particles. As such material, synthetic material such as polyester and glass fiber filter can be used. Commonly, glass fiber and polyester produced by S & S are used. Since these are biologically inactive and have more delicate fibrous material than natural material, they are not distorted or swollen when an aqueous reagent or sample is applied. Preferably, the conjugate releasing pad is pretreated with a reagent such as a surfactant so that an analyte is prevented from non-specifically binding to the fluorescently-labeled detector on the releasing pad and the conjugate can smoothly be released and migrate.

Methods for attaching a reagent onto the conjugate releasing pad include an impregnation process in which a pad such as glass fiber is immersed in a solution of a high density reagent particularly formulated, followed by drying. However, the impregnation process has several simple problems. Firstly, the pad can be crumpled or distorted during dehydration. Secondly, during drying the pad in an oven, reagents may be separated from the pad or reconstituted due to surface tension and gravimetric action according to location on the pad. Thirdly, chemical changes of reagents may take place with the passage of time in the immersion bath, causing the reagents to have different adsorption rates, whereby the reagents are unevenly coated on the pad. One method to minimize these problems is to perform drying of the pad in an oven at less than 40° C. for several hours. Another method is to lyophilize the pad instead of drying the pad in an oven. Such lyophilization is preferred to drying in the oven in that stability of the detector can be secured.

As an alternative method to the impregnation process, a dispensing process may be used. This process involves dispensing 12 to 15 µl of a reagent solution per cm of the pad using a dispenser and drying it. The drying of the pad is carried out the same as in the impregnation process. Also, the pad may be lyophilized.

Furthermore, the conjugate releasing pad may be treated with a stabilizing agent and shielding agent. Examples of the stabilizing agent include saccharides such as sucrose, trehalose, etc. Examples of the shielding agent include proteins such as BSA (Bovine Serum Albumin), gelatin, casein, skim milk and the like, but are not limited thereto.

Chromatography Medium of the Lateral Flow Assay Strip

The material of the chromatography medium may be any one that can allow the fluid sample and conjugate to rapidly move via capillary action to reach the captor immobilized thereon and preferably has homogeneous properties. Typically, the chromatography medium refers to a porous material having a pore diameter of at least 0.1µ, preferably 1.0µ and through which an aqueous medium can readily move via capillary action. Such material generally may be hydrophilic or hydrophobic, including for example, inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross-linked dextran, agarose, polyacrylate, etc.; either used by themselves or in conjunction with other materials. Also, ceramics may be used. The chromatography medium can be bound to the backing. Alternatively, the chromatography may be the backing per se. The chromatography medium may be multifunctional or be modified to be multifunctional to covalently bind to the captor.

When using a high concentration of the captor chemically binding to the chromatography medium so as to react and trap the analyte/detector conjugate migrating from the conjugate releasing pad, preferably, an activated filter paper sheet is used as the chromatography medium. When a CNBr activated cellulose is selected as the material for the filter paper, an activated cellulose filter paper sheet can be easily prepared by a known method such as the method described by Ceska and Lundkvist (Immunochemistry, 9, 1021 (1972)). When the material is DBM activated cellulose, it can be easily prepared by a known method such as the method described by Alwine (Methods Enzymol., 68, 220 (1979)). Further, a commercially available activated nylon film (Pall Immunodyne, USA) may also be used.

One of the important properties of the chromatography medium is its capacity to immobilize a captor. Such binding capacity is varied depending upon a pore structure of the medium and a post-treatment which the medium undergoes. A preferred chromatography medium which can be used in the present invention is a nitrocellulose (NC) membrane and examples thereof are described in Table 1 below.

TABLE 1

| Supplier | Product | Sec/4 cm (flow rate$^{(a)}$) | IgG/cm$^{2(b)}$ |
|---|---|---|---|
| S&S | AE 98 | 160-210 | 20-30 ug |
| (without a backing) | AE 99 | 120-160 | 20-30 ug |
|  | AE 100 | 90-120 | 20-30 ug |
| Millipore | HF 090 | 80-100 | >95 |
| (with a backing | HF 120 | 107-133 | >95 |
| bound) | HF 135 | 120-150 | >95 |
|  | HF 180 | 160-200 | >95 |
|  | HF 240 | 214-266 | >120 |
| Sartorius | CN 90 | 88-94 | 10-30 |
| (with a backing | CN 140 | 137-153 | 10-30 |
| bound) | CN 200 | 206-233 | 10-30 |

$^{(a)}$time for distilled water to move on the medium by 4 cm
$^{(b)}$maximum binding capacity of IgG per cm$^2$ In the table, the most preferred membrane is CN 90 membrane. This membrane has the smallest variation in flow rate among the described products. The binding capacity on the order of 10 to 30 ug is sufficient since amplification of fluorescent substances is excellent.

The captors are immobilized on the chromatography medium via chemical bonding. The chemical bonding is carried out according to a known method (LABORATORY TECHNIQUES IN BIOCHEMISTRY AND MOLECULAR BIOLOGY, Volume 15, Edited by R. H. BURDON and P. H. Van KNIPPENBERG ELSEVIER AMSTERDAM: NEW YORK, OXFORD (1985) P. 318-322). Further, the captor may be bound to the activated paper sheet through a second substance (ex. antibody protein, etc.). When the second substance present therebetween is an antibody (to be referred to as "second antibody" hereinafter), and for example, when the captor to be fixed is a monoclonal antibody derived from mouse, there may be used the activated paper sheet to which an excess of anti-mouse γG (gamma globulin) hetero-animal antibody is bound and then a proper amount of the captor is bound by an immunoreaction. When the substance present therebetween is a protein, for example, there may be used the activated paper sheet to which an excess of protein A is bonded and then a proper amount of the trapping antibody is bound.

In order to uniformly wet test lines within the viewing window on the chromatography medium, a blocking technique is used. By blocking the chromatography medium with a material which can enhance rewetting of the chromatography medium, it is guaranteed that the medium can be rewetted uniformly and rapidly. There are four kinds of blocking material: proteins such as BSA and gelatin; surfactants such as SDS, Tween 20 and Triton X-100; polymers such as PVA, PEG and PVP. These blocking materials can be used at three points. Firstly, they can be applied directly onto the chromatography medium. This method can provide highly uniform rewetting effects. However, the blocking should be performed after immobilization of the captors but before adhesion of the sample pad. This method requires use of expensive coating equipments. Also, the captors should be redissolved and moreover, the blocking material may deteriorate the antigenicities and storage life of the captors. Secondly, the blocking material may be incorporated into the sample pad or conjugate releasing pad. This method has merits in that it can be readily performed at low cost and re-dissolution of the captors is not needed, but its blocking effect is not satisfactory. This method is preferable in terms of easiness of handling though it has a blocking efficiency inferior to the first method. Thirdly, the blocking material can be added to a buffer solution to apply the captor on to the chromatography medium. This method also has merits in that it can be readily performed at low cost and re-dissolution of the captors is not needed. However, it has disadvantages that the captors tend to diffuse away, the antigenicities and storage life of the captors may be lowered due to the addition of the blocking agent.

In order to prevent non-specific binding of the reagents used in the sample pad, conjugate releasing pad and chromatography medium, two types of methods may be used. One is to immerse the chromatography medium to which the captors have been applied in a solution containing proteins or a highly polar polymer such as polyvinyl alcohol or to spray such solution to the chromatography medium to block up the non-specific binding sites on the chromatography medium. However, this method may cause substitution of captors, particularly when the captors are not optimally immobilized by complete drying before the blocking step. The other method is to add a blocking agent to the sample pad. In this case, the blocking agent does not, at least initially, interfere with the binding of captors to the chromatography medium. When the liquid sample is applied to the sample pad, the blocking agent on the sample pad is resolubilized in the sample pad, to thereafter move together with the sample. Ideally, a sufficient amount of a blocking agent is added to the sample pad to block all non-specific bindings of all the analytes and detectors.

Figure 17:
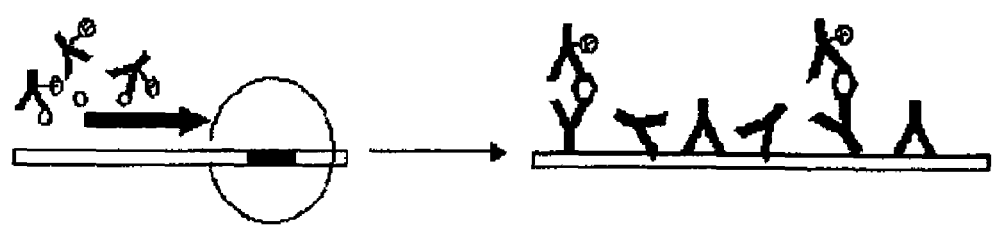
FIG. 17 is a schematic view of the bound reactants in the test line region on the strip when using the biotin-avidin system according to the present invention and the conventional method.
Figure 17:
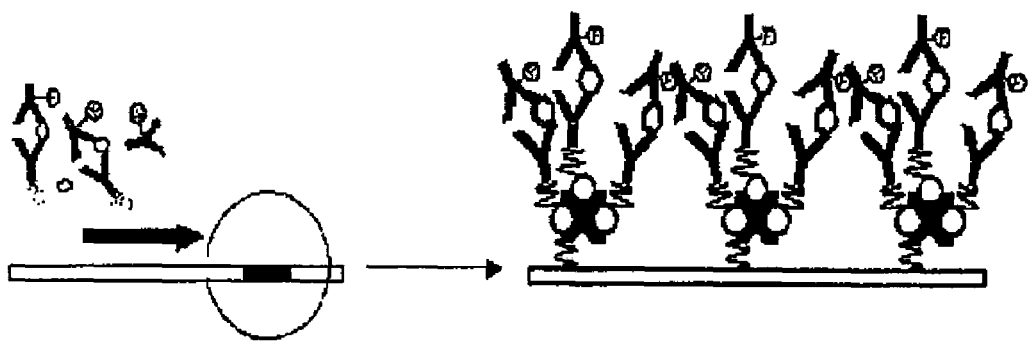
Figure 18:
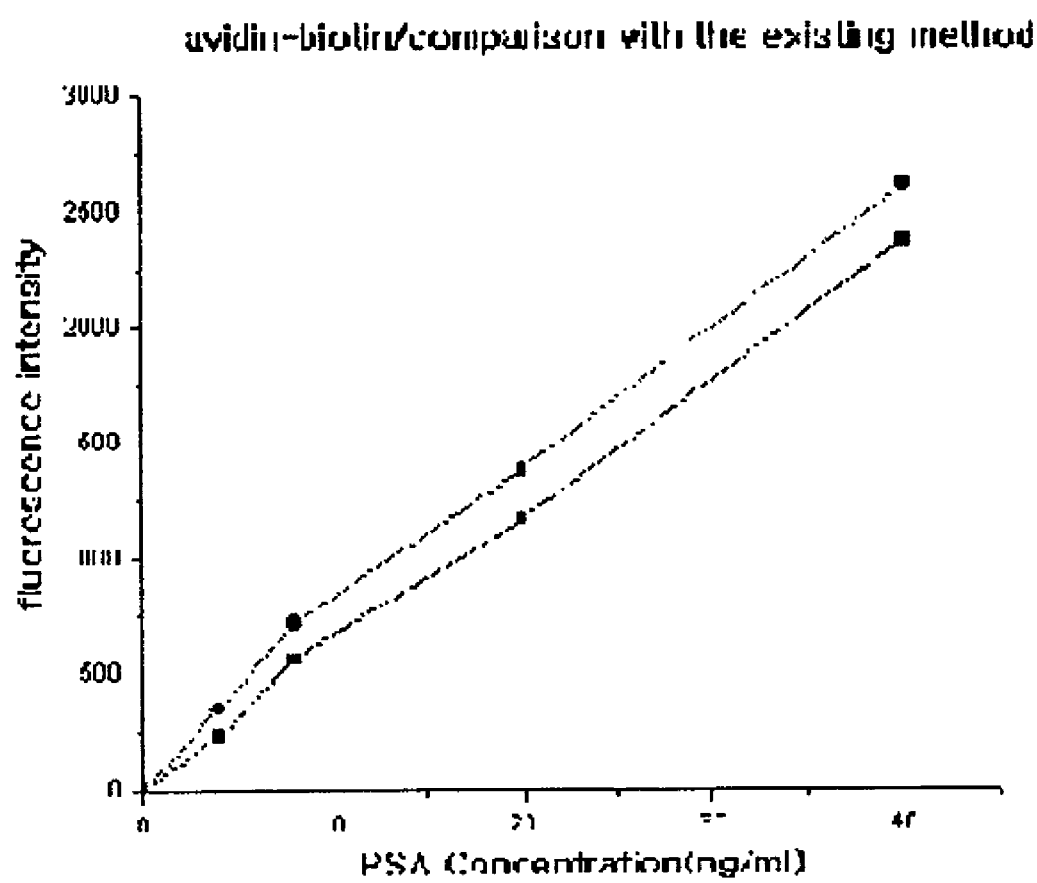
FIG. 18 is a graph showing the results of quantification using the biotin-avidin system according to the present invention and the conventional method.

According to the preferred embodiment of the present invention, biotin-avidin conjugate is used as an analyte capture system. That is, avidin is added onto and immobilized on the test line of the strip instead of a captor (ex. antibody or antigen protein). Biotin is attached to the captor. As the biotin binds to the avidin, the captor can be automatically detected on the test line of the strip. When the captor is a protein, the binding of the biotin to the captor is effected by reacting with an amine group of lysine or arginine among amino acids. Thus, the biotin is specifically bonded to a certain site of the protein via an amine group of such amino acids. The protein with biotin attached specifically binds to the avidin which has been planted and immobilized on the strip and always maintains one orientation. Further, since the captor is not fixed via adsorption, the protein of the captor is not changed in structure or functions thereof. For these reasons, unlike the conventional method by which the captor is immobilized non-specifically on the layer of the strip without maintaining a particular orientation, according to the biotin-avidin method, the captor protein can be immobilized in one direction, and thereafter always maintain the orientation. Also, since the proteins of the captors are not changed in their structure or functions by the adsorption, they can more effectively react with the analytes in the test sample. Therefore, the biotin-avidin method can exhibit much higher sensitivity at the same concentration of an analyte compared to the conventional method. Even when an analyte is present at a concentration 10 to 100 times lower than the immobilized captor in the conventional method, a high sensitivity can be attained. Further, with an avidin-immobilized strip, when a different analyte is examined, there is no need for preparing a new strip of a different type. Only different protein-biotin conjugates and protein-fluorescently labeled conjugates as detectors are needed to assay various analytes. The method according to the present invention can be performed using a strip having the conjugate pad as in the conventional method, but also can be performed by directly adding analytes, protein-biotin conjugates, and protein-fluorescent conjugates in a solution to the sample pad without a conjugate pad. FIG. 17 shows the schematic diagram of the method using the biotin-avidin system on the test line of the strip and the conventional method.

Absorption Pad of the Lateral Flow Assay Strip

The absorption pad is means for physically absorbing the sample which has chromatographically moved through the chromatography medium via capillary action and for removing unreacted substances. Thus, the absorption pad is located at the end of the lateral flow assay strip to control and promote movement of samples and reagents and acts as a pump and container for accommodating them. The speeds of samples and reagents may vary depending on the quality and size of the absorption pad. Commonly used absorption pads are formed of water-absorbing material such as cellulose filter paper, non-woven fabric, cloth, or cellulose acetate.

Wicking Pad of the Lateral Flow Assay Strip

The wicking pad is used to improve diffusion of a sample such as blood and prevent contamination of the conjugate pad by microorganisms during storage. Commonly, AW14-20T4, hydroxylated polyester, produced by Pall Corporation (USA) is used.

Now, the lateral flow assay strip according to the present invention will be more concretely described while referring to the appended figures. From this description, the features and advantages of the present invention will become more apparent.

Figure 3:
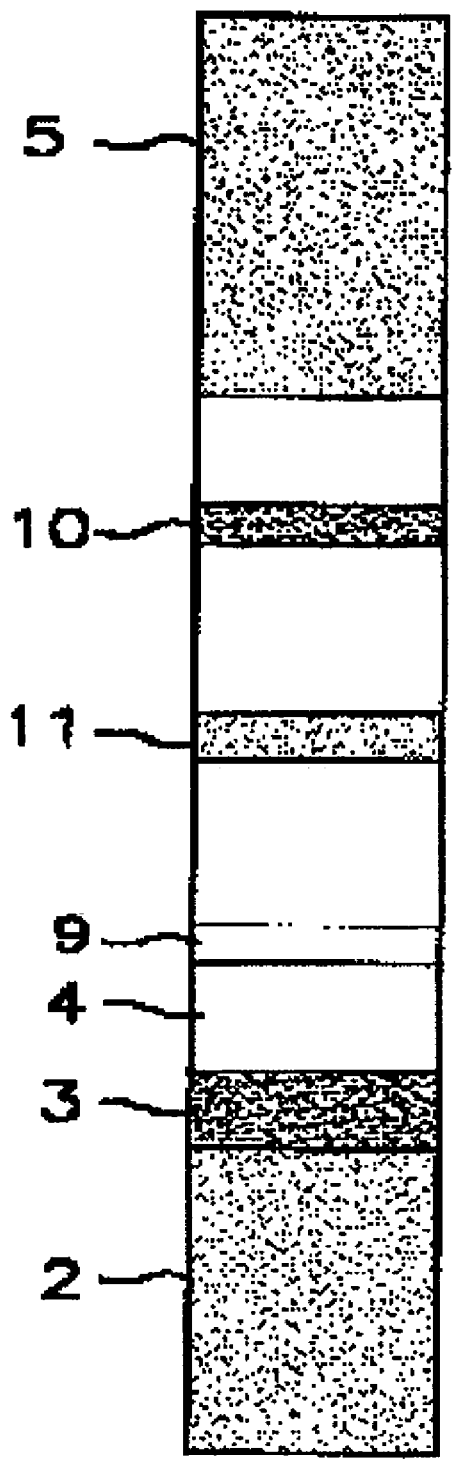
FIG. 3 is a plan view of the conventional lateral flow quantitative assay strip shown in FIG. 1.

FIG. 1 and FIG. 3 show the conventional lateral flow assay strip. Referring to FIG. 1, the lateral flow assay strip 1 includes a sample pad 2 attached to one end of a backing 6 via an adhesion layer, upon which a liquid sample containing an analyte is applied, and successively, a conjugate releasing pad 3, a chromatography medium 4 and an absorption pad 5 toward the opposite end of the sample pad. On the conjugate releasing pad 3, a labeled detector is releasably attached so that the analyte in the liquid sample chromatographically moving via capillary action can react with the detector to form conjugate. On the chromatography medium 4, a captor which is identical to or different from the detector is immobilized in a line (test line) 11 by chemical bonding. The captor in the line 11 chemically reacts with the liquid sample and the conjugate formed on the conjugate releasing pad 3, which have been chromatographically moving on the strip, trapping the conjugate to form a labeled detector/analyte/captor conjugate. Remaining unreacted substances and the liquid sample continuously move by capillary action on the strip and are absorbed by the absorption pad 5. The amount of the analyte is determined by measuring the amount of the conjugate. The amount of the conjugate is determined as a relative value by comparing a luminescent intensity of the conjugate trapped on the chromatography medium with a reference luminescent intensity which is obtained from a conjugate formed of a reference detector which has been labeled identically with the analyte detector, and is different from the analyte detector and captor, and a reference captor which is not labeled and is different from the reference detector.

As described above, the conventional lateral flow assay strip is designed with the intention of quantitatively analyzing only one kind of an analyte in a biological sample.

Figure 2:
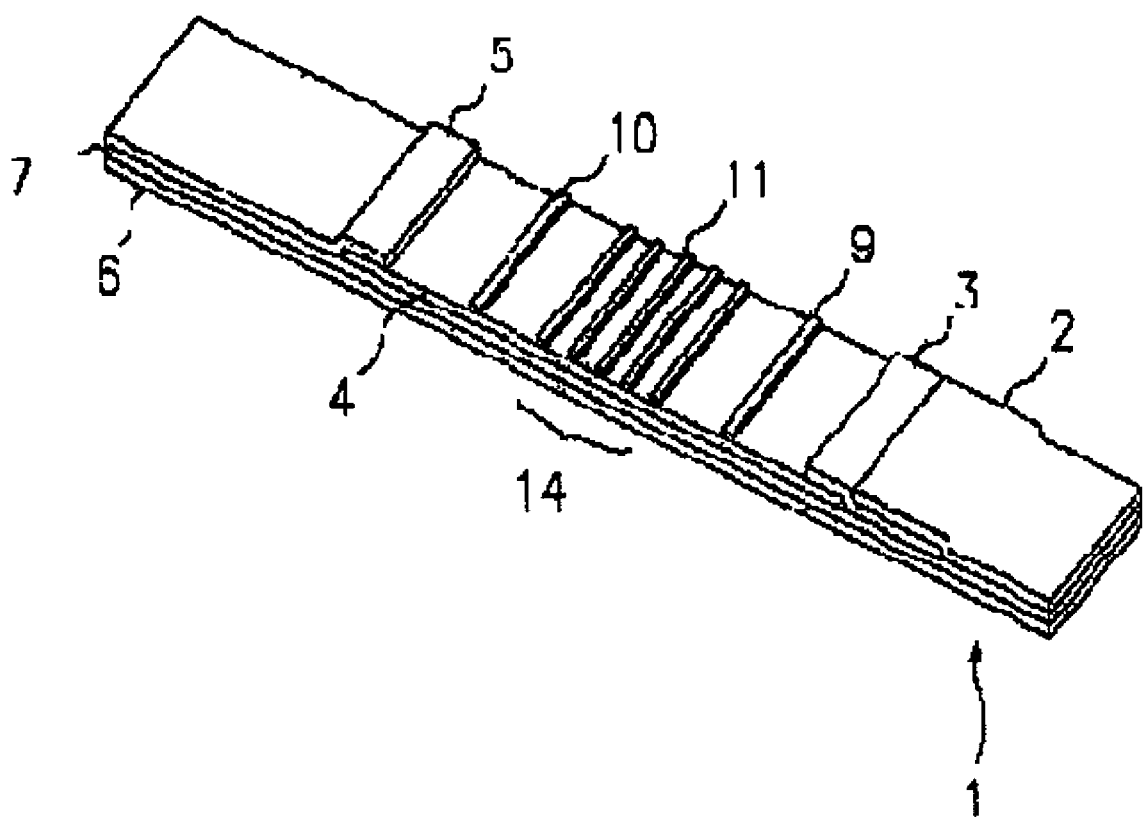
FIG. 2 is a perspective view of the lateral flow quantitative assay strip of an embodiment according to the present invention.
Figure 4:
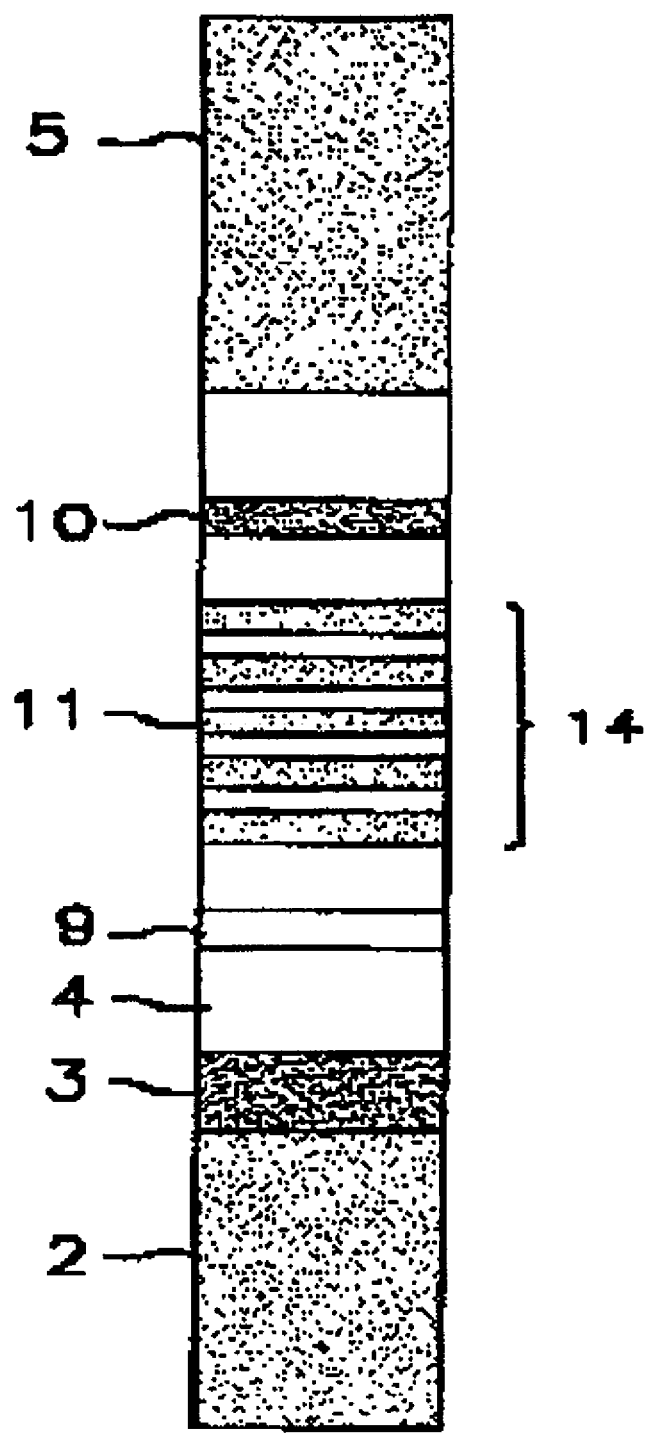
FIG. 4 is a plan view of the lateral flow quantitative assay strip of the embodiment according to the present invention shown in FIG. 2.
Figure 5:
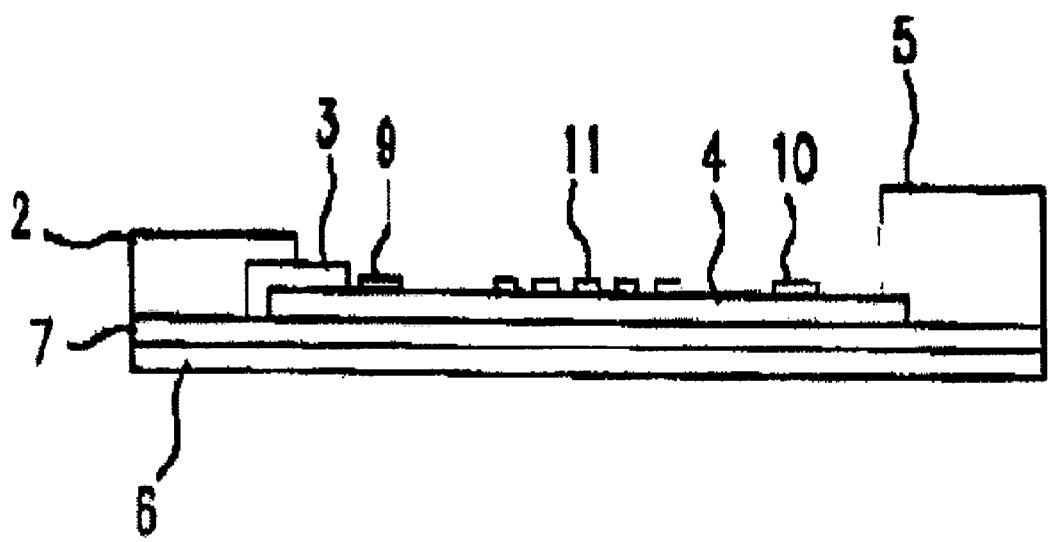
FIG. 5 is a side view of the lateral flow quantitative assay strip of the embodiment according to the present invention shown in FIG. 2 and FIG. 4.

FIG. 2, FIG. 4 and FIG. 5 show a lateral flow quantitative assay strip of an embodiment according to the present invention. The lateral flow assay strip has a construction in which four or more kinds of detectors are releasably attached on the conjugate releasing pad 2, and various captors in the same number as the kinds of the detectors are immobilized in micro test lines 11, whereby it is possible to assay diverse analytes at the same time. Here, each kind of captor is immobilized in an individual test line and hence, the number of the test lines are the same as the number of the kinds of captors. That is, it is possible to assay as many analytes as the number of the test lines. The number of the test lines can be restricted by the size of the strip, kinds and amounts of reagents (detectors and captors) used in the strip, required sensitivity, etc. According to the present invention, the strip has generally 2 to 20 test lines, preferably 5 to 15 test lines.

Figure 6:
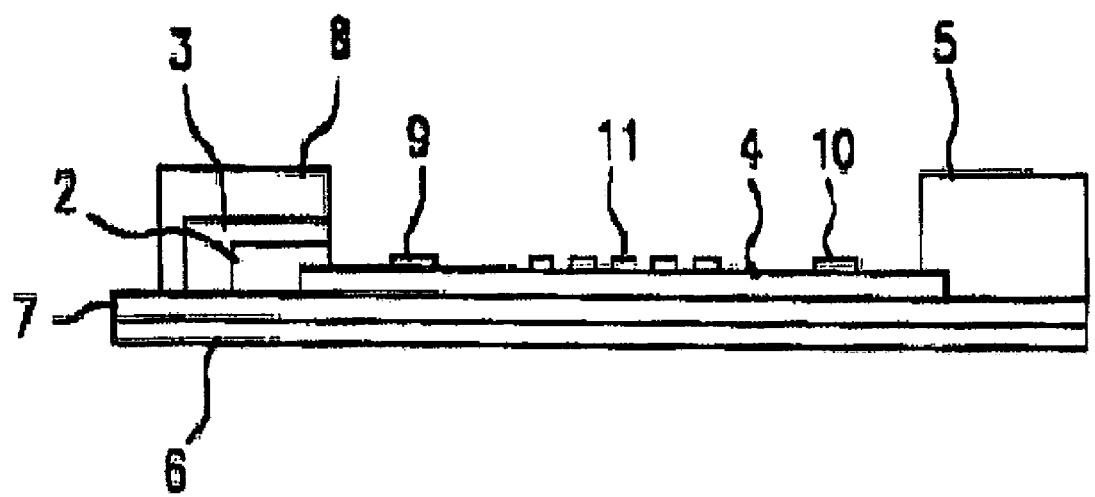
FIG. 6 is a side view of a lateral flow quantitative assay strip of another embodiment according to the present invention.

FIG. 6 is a lateral flow quantitative assay strip of another embodiment according to the present invention. The lateral flow quantitative assay strip as shown in FIG. 6 includes a sample pad 2 disposed on a chromatography medium 4, a conjugate releasing pad 3 disposed on the sample pad 2 and a wicking pad 8 disposed on the conjugate releasing pad 3. The wicking pad 8 mounted on the conjugate releasing pad 3 is to facilitate dispersion of the liquid sample, to enhance the solubility of the conjugate releasing pad and to protect detectors and reference detectors which are releasably attached to the conjugate releasing pad from being modified or damaged by microbial contamination during storage of the strip.

The representative wicking pads which are useful according to the present invention are ones formed of hydroxylated polyesters, but are not limited thereto. Among examples of such hydroxylated polyesters is AW14-20T4, produced by Pall Corporation (USA).

After application to the wicking pad 8, the liquid sample is dispersed while passing through the wicking pad 8 and diffused to the conjugate releasing pad 3, upon which detectors and reference detectors releasably attached to the conjugate releasing pad 3 are dissolved in the liquid sample and react with analytes in the sample, forming conjugates. The conjugates along with the liquid sample then reach the sample pad 2. The sample pad 2 disposed under the conjugate releasing pad 3 acts as supplementary means, in which the analytes in the liquid sample which have not yet formed conjugates can sufficiently reacts with unreacted reagents. Also, the sample pad 2 acts as buffering means so that the liquid sample and conjugates can smoothly moves to the chromatography medium 4. Next, the formed conjugates moves to the chromatography medium along with the liquid sample which moves to the chromatography medium via capillary action, to be trapped by reagents (captors and a reference captor) which are immobilized in test lines on the chromatography medium.

Figure 7:
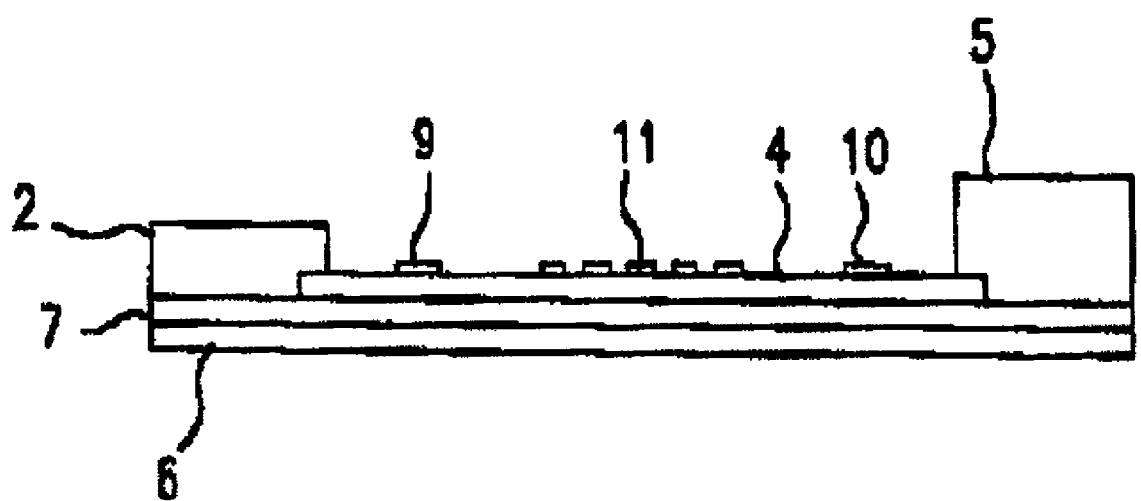
FIG. 7 is a side view of a lateral flow quantitative assay strip of another embodiment according to the present invention.

FIG. 7 is a lateral flow quantitative assay strip of yet another embodiment according to the present invention. This strip is only provided with a sample pad 2 on a chromatography medium 4. Here, the sample pad 2 also can serve as a conjugate releasing pad since fluorescently-labeled detectors and a reference detector are releasably attached to it. The formed conjugates formed on the sample pad move to the chromatography medium along with the liquid sample which moves through the chromatography medium via capillary action, to be trapped by reagents (captors and a reference captor) which are immobilized in test lines on the chromatography medium.

In another mode, the sample pad does not have detectors and a reference detector attached to it. In this case, a liquid sample is applied on the sample pad in a two-step process, by which the liquid sample is mixed with fluorescently-labeled detector and a reference detector and the mixture is applied to the sample pad. This two-step process provides effects of increasing the sensitivity of the assay by a factor of two or more compared to the method in which the fluorescently-labeled detector and a reference detector are attached to the sample pad. However, it has a disadvantage in that the detectors should be stored in a refrigerator before use, causing problems in portability. Analytes in the liquid sample react with the detectors to form conjugates. The formed conjugates moves to the chromatography medium along with the liquid sample which moves to the chromatography medium via capillary phenomenon, to be trapped by reagents (captors and a reference captor) which are immobilized in test lines on the chromatography medium.

Figure 8:
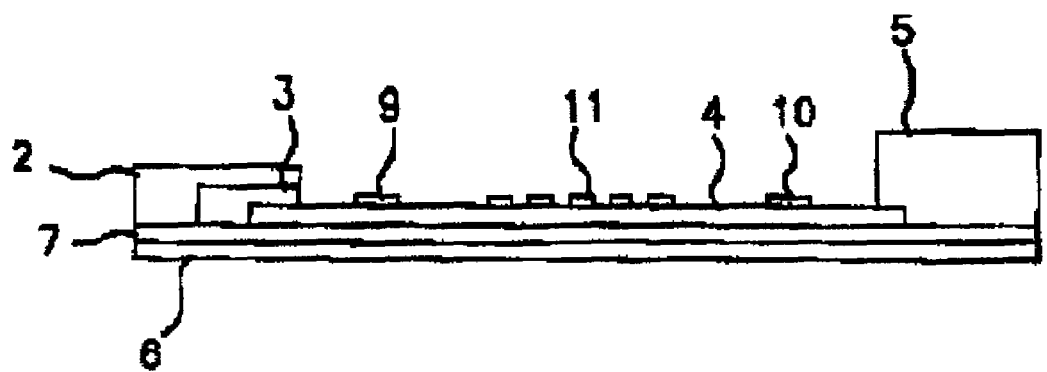
FIG. 8 is a side view of a lateral flow quantitative assay strip of another embodiment according to the present invention.

FIG. 8 is a lateral flow assay strip of yet another embodiment according to the present invention. This lateral flow assay strip includes a conjugate releasing pad 3 disposed on a chromatography medium and a sample pad 2 disposed at a fixed position on the conjugate releasing pad 3. After application to the sample pad 2, the liquid sample migrates to the conjugate releasing pad 3 by diffusion, upon which analytes if present in the liquid sample react with fluorescently-labeled detectors, forming conjugates. The formed conjugates moves to the chromatography medium along with the liquid sample which moves to the chromatography medium via capillary action, to be trapped by reagents (captors and a reference captor) which are immobilized in test lines on the chromatography medium.

Figure 9:
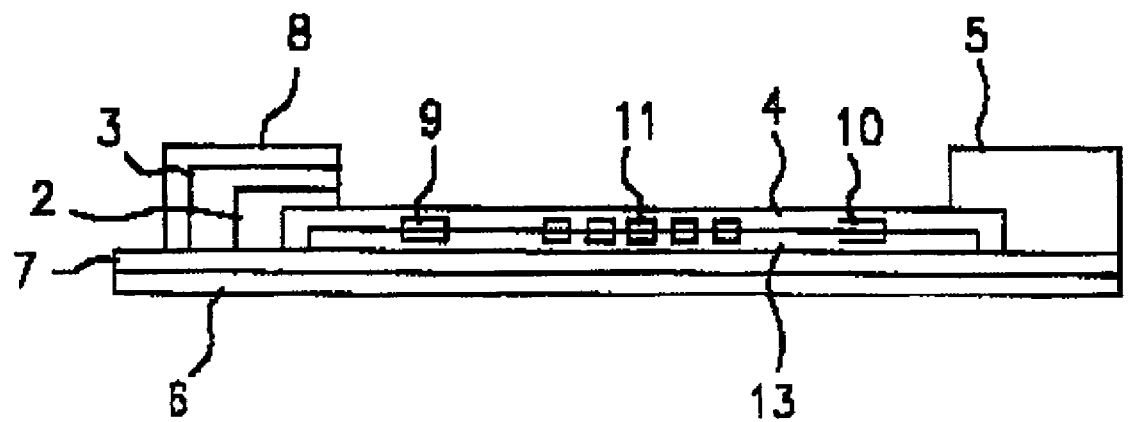
FIG. 9 is a side view of a lateral flow quantitative assay strip of another embodiment according to the present invention.

FIG. 9 is a lateral flow assay strip of yet another embodiment according to the present invention. This lateral flow assay strip is the same as that shown in FIG. 6, except that it has two layers of chromatography mediums laminated together. A second chromatography medium 13 is adhered to an adhesive layer 7 on a backing 6 and a first chromatography medium 4 is disposed on the second chromatography medium 13, extending over both ends of the second chromatography medium 13, in which the extended ends of the first chromatography medium 4 are adhered to the adhesive layer 7 on the backing 6. On the first chromatography medium 4, a sample pad 2 and an absorption pad 5 are disposed at its opposite ends, respectively.

Captors 11 and reference captors 9,10 are immobilized at the upper and lower part, respectively, of the interface between the first chromatography medium 4 and the second chromatography medium 13. Here, the captors immobilized at the bottom of the first chromatography medium may be identical to or different from the reference captors immobilized at the top of the second chromatography medium. If identical reference captors are immobilized on the interface between the two chromatography media, the sensitivity is increased by at least two times, compared to when the reference captors are immobilized on one chromatography medium. If different reference captors are immobilized on the interface between the two chromatography media, it is possible to assay twice the number of analytes compared to when identical reference captors are immobilized on the interface between the two chromatography media, and when the reference captors are immobilized on one chromatography medium.

Also, this type of lateral flow assay strip may be advantageous in that it can be stored for an lengthy period of time while maintaining its sensitivity, since the reagents are not exposed to the outside.

Figure 10:
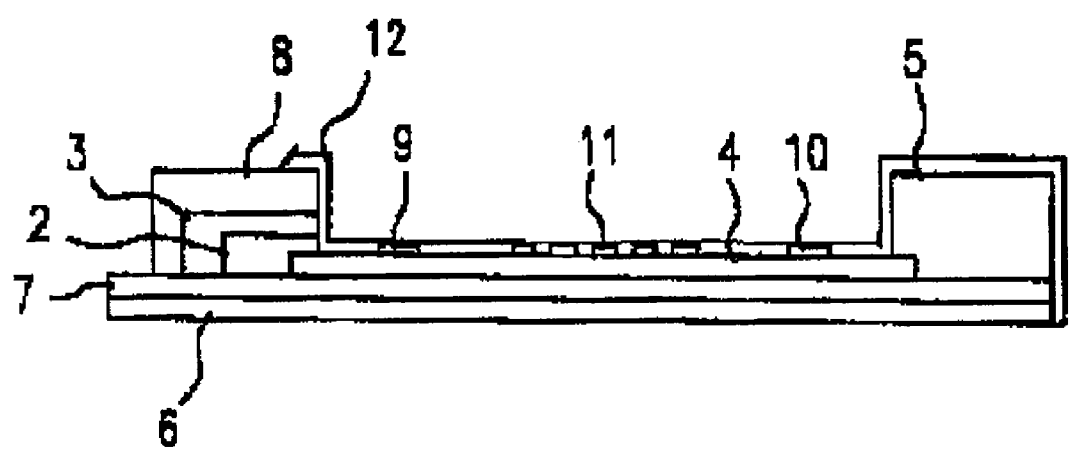
FIG. 10 is a side view of a lateral flow quantitative assay strip of another embodiment according to the present invention.

FIG. 10 is a lateral flow assay strip of yet another embodiment according to the present invention. This lateral flow assay strip includes a thin and transparent polyester film on the lateral flow assay strip shown in FIG. 6. By laminating a polyester film on the top of the strip, it is possible to reduce the background signal by labeling due to water evaporation occurring during the test and thus to maintain a high sensitivity. Also, the top of the strip which is exposed to the atmosphere during testing or storage can be protected from moisture and airborne contaminants by the laminated polyester film, thereby providing a consistent quality. Further, an acryl adhesive tape can be adhered to the top of the strip, which can solidly integrate the pads adhered to the backing of the strip in addition to the foregoing effects obtained by the polyester film.

Figure 11:
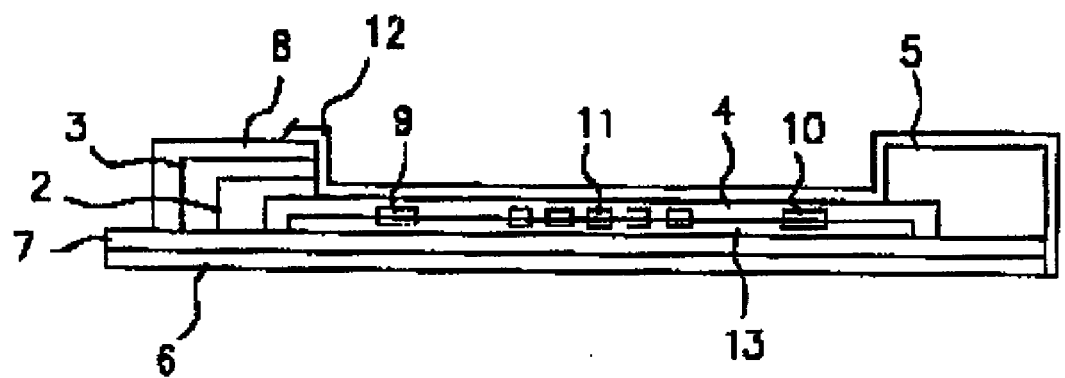
FIG. 11 is a side view of a lateral flow quantitative assay strip of another embodiment according to the present invention.

FIG. 11 is a lateral flow assay strip of yet another embodiment according to the present invention. This lateral flow assay strip further includes a thin and transparent polyester film or an acryl adhesive tape on the top of the lateral flow assay strip shown in FIG. 9. This type of strip provides the advantages of the lateral flow assay strips shown in FIG. 9 and FIG. 10, thus being very preferred.

Laser-Induced Epifluorescence Detecting Apparatus

The present invention, in general, relates to a method for detecting laser-induced epifluorescence and a device therefor. More particularly, the present invention relates to a method for detecting epifluorescence by using an elliptical or spherical reflecting mirror which can effectively collect fluorescence emitted when irradiating laser or light with a proper wavelength to a fluorescent substance attached on the surface of an opaque sample transparent and a device therefor.

A representative method used for detecting fluorescence of DNA chips or protein chips using membranes is laser-induced fluorescing detection. The laser-induced fluorescing detection involves rendering a fluorescent material to be an excited state using a laser as a excitation light source and measuring the intensity of fluorescence emitted when the material returns to the ground state, in which the fluorescence intensity can be converted to a concentration of the material. Thus, it is possible to quantify DNA or protein sample by attaching a fluorescent material.

One of the most commonly used detectors which apply the laser-induced fluorescence detection is a confocal laser scanning system. In this system, a laser is used as a light source and fluorescent signals emitted from a specimen are focused on to a photomultiplier tube as a separate special detector, in which the signals are converted into digital images. Thus, the confocal laser scanning system irradiates a light of only the wavelength range suitable for the fluorescent material labeling the specimen using a laser to induce emission of fluorescence. In this case, various kinds of filters such as a beam splitter can be selected and a pinhole is located at the last position in front of the detector so that the detector receives only the image being in complete focus (FIG. 1). Meanwhile, when using the confocal laser scanning system, it requires to use a cover glass of a proper thickness and to select a suitable object lens and mounting medium. It has an advantage that images being out of focus can be removed.

In laser-induced fluorescence detection devices and technologies at the present time, it is important to improve the sensitivity of the fluorescence detectors. One of the main factors in improving the sensitivity of the fluorescence detectors is to collect maximum fluorescing radiation, while minimizing the background, i.e., collected excitation light intensity).

Therefore, in order to obtain optimum detection limit in a laser-induced fluorescence detector, the fluorescence generated from a fluorescently-labeled sample must be collected with high efficiency, while scattered excitation light reaching the detector must be minimized. In practice, high aperture value objectives or reflectors may be used to collect fluorescence. The fraction of light collected by a lens is related to the aperture value of the lens, and refractive index of the surrounding medium. This relationship may be expressed by the following equation:

$$\text{Collection Efficiency} = \sin^2(\sin^{-1}NA) = \sin^2(\sin^{-1}(1/2F))$$

In the above equation, F represents the aperture value (F number) and NA represents numerical aperture. Collection efficiency of 1 implies that the lens collects all of the light emitted by the sample.

Usually, the light collecting lens is surrounded by air, which has a refractive index of 1. From the above equation, it can be seen that a lens of a very small aperture value is required to obtain high collection efficiency. A lens with an aperture value of 1 will collect 50% of the light emitted by the sample. Although lenses immersed in a liquid medium (oil, water, etc.) can have an aperture value less than 1, they collect less than 50% of the emitted light because the refractive index of the immersion fluid is usually larger than the refractive index of the lens material. In addition, according to the above equation, a lens with an aperture value of 0.5 and located in air collects only 7% of the emitted light. In deed, it is impossible to have an aperture value of 0.5.

In the conventional arts, refractive and/or reflective optical collectors are utilized in laser-induced fluorescence detectors with or without optical fibers for collecting the emitted fluorescing radiation. However, the capability of these collectors collecting fluorescence light is limited by their maximum collection angle. A typical high collector will have a collection cone angle of about 90°. This corresponds to a 0.7 numerical aperture, or 14% collection efficiency.

U.S. Pat. No. 5,614,726 issued to Kaye et al. on Mar. 5, 1997 disclosed a laser-induced fluorescence detector. However, the detector has a collection efficiency of only 6 to 7%.

Therefore, there exists a need to develop a improved laser-induced fluorescence detector that has a higher collection efficiency optics and enhanced signal strength in detection of epifluorescence of lateral flow assay strips and biochips such as DNA chips or protein chips using membranes.

According to the present invention, in order to measure epifluorescence to determine quantities of analytes, a laser-induced epifluorescence detecting apparatus is used, which comprises a laser, an exciter filter, an elliptical reflecting mirror or spherical mirror, epifluorescence sample control means, a collimator, a fluorescent filter and an optical detector, in which the components are arranged in a structure such that light emitted from a laser is passed through the exciter filter and focused to the surface of a sample, in which the focusing point is the first focal point of the elliptical reflecting mirror with a proper size, scattered light of the incident light and fluorescence emitted from the first focal point are reflected from the elliptical reflecting mirror and focused upon a spatial filter as the second focal point of the elliptical reflecting mirror, and the light from the spatial filter is converted into parallel light by a collimator and passed through a fluorescent filter to remove the scattered light, thereby providing a pure fluorescence component to the optical detector.

A conventional lateral flow assay strip comprises a sample pad, to which a sample is applied, a releasing pad coated with a detector antibody, a developing strip (typically, nitrocellulose), in which components of the sample move at different rates to be individually separated and to undergo antibody-antigen reaction and an absorption pad provided at the far end of the sample pad to cause the sample to keep moving. Particularly, the lateral flow assay strip has a sample pad 2 attached to one end of a support via an adhesion layer, upon which a liquid sample containing an analyte is applied, followed by a conjugate releasing pad 3, a chromatography medium 4 and an absorption pad 5 toward the opposite end of the sample pad. On the conjugate releasing pad, a first fluorescently-labeled detector is releasably attached so that the analyte in the liquid sample, while chromatographically moving via capillary action, can react with the detector to form conjugate. On the chromatography medium, a second captor which is identical to or different from the first detector is immobilized in a single line (test line) by chemical bonding. The captor in the single line chemically reacts with the liquid sample and the conjugate formed on the conjugate releasing pad, which have been chromatographically moving on the strip, trapping the conjugate. Remaining unreacted substances and the liquid sample continuously move by capillary action on the strip and are absorbed by the absorption pad. The amount of the analyte is determined by measuring the amount of the conjugate, which is determined as a relative value by comparing a luminescent intensity of the conjugate trapped on the chromatography medium with a reference luminescent intensity which is obtained from a conjugate formed of a third detector which is different from the first detector and the second captor and has been labeled identically with the first detector and a unlabeled forth captor which is different from the third detector.

DNA chip refers to an array of hundreds to hundreds of thousands of DNAs packed in a very small space by mechanical automation and electronic control. In other words, the DNA chip is a biological chip constructed by binding DNAs to a small substrate of glass, silicone, or nylon to analyze gene expression aspects, gene binding, protein distribution, reaction aspect, etc. The DNA chips are classified into cDNA chips and oligonucleotide chips according to the size of genetic substance binding to a substrate. The cDNA chips have genes (full-length open leading frame) of at least 500 bp while the oligonucleotide chips have oligonucleotides of about 15 to 25 bp.

Techniques for manufacturing DNA chips using target DNA are largely divided into two types: one is to directly synthesize oligonucleotides on a substrate and the other is to plant synthesized or amplified target DNA onto a substrate. The former applies the photolithographic method derived from manufacturing method of semiconductor chips and has an advantage that it can accomplish high-density integration. However, the size of the target DNA is limited to 20 nucleotides. It is suitable for disease diagnosis or research of single nucleotide polymorphism (SNP). The latter DNA chip is applied in researches of differential gene expression. The target DNA is planted on a slide coated with poly L-lysine, amine or aldehyde.

Methods for plotting DNA include the micropipetting using a piezoelectric method. Spots have a diameter of about 100 μm and distributed at a ratio of about 1000 spots/cm$^2$.

Methods for labeling nucleic acid in a DNA chip are largely divided into direct labeling and indirect labeling though there are diverse methods. The direct labeling involves direct insertion of fluorescent tags into a probe mixture of nucleic acid to be hybridized in a DNA chip by enzyme synthesis. The direct labeling has merits that it is simple, provides strong hybridization signal and can use other dyes having similar chemical structures but different in their absorption or emission wavelengths. Such merits are important, particularly in comparative analyses, because a fluorescent material having a much different structure may cause an erroneous result in a differential gene expression experiment. In the direct labeling, it is necessary to use different kinds of fluorescent materials for maximization of precision in a comparative analysis. For DNA chips, chemically related dyes such as cyanine and alexa analogs are used. The indirect labeling is accomplished by inserting an epitope into a probe mixture of nucleic acid. After hybridization of tagged nucleic acid with the epitope, the DNA chip stains proteins bound to the epitope. By virtue of the stained protein, fluorescent signal can be obtained. One of general examples of the indirect labeling is to use the binding of biotin epitope and fluorescent streptavidin-phycoerythrin. The greatest advantage of the indirect labeling is that signal amplification increases 10 to 100 times higher, compared to the direct labeling. Capital shortcomings of the indirect labeling are that it is difficult to be performed, the epitope has different labeling efficiencies and the precision is poor in comparative analyses due to the binding force of proteins.

A format of the most commonly used DNA chips is a 1"×3" microscope slide. Since it has a large surface area (approximately 19-cm$^2$), it can produce 100,000 or more arrays using microspotting and ink-jetting techniques. Also, due to the peculiarly low fluorescence intensity of glass per se, it can be favorably used. In addition, a cassette, produced by Affymertix is widely used as a DNA chip format. The cassette of affymertix is enclosed in a plastic frame to protect a glass chip.

According to the present invention, it is possible to produce very abundant data from a DNA chip, which can serve as a basis of bioinformatics. Data can be applied to a modeling, yielding much information via computational biology. Quantified data from DNA chips are displayed by various methods, among which a representative method is a scatter plot. Plots of the whole data obtained from a two-color experiment are expressed as a function of ratio and signal intensity. When the ratio is greater than 1.0, the result is plotted above the diagonal where the ratio is 1.0 and when the ratio is less than 1.0, the result is plotted below the diagonal. This method can be used as means to survey a huge database such as thousands of gene expression profiles. Commonly, with one mouse click of a spot on a computer screen, information of the gene sequence corresponding to the spot in the DNA chip is displayed.

In another aspect of the present invention, there is provided a method for detecting epifluorescence emitted from a protein chip. Preparations and applications of the protein chip are well-known to those skilled in the art and diversely described in numerous science journals and patents. For example, the protein chip comprises antibodies against proteins associated with various diseases which are integrated on a small substrate. It can diagnose early presence and progress of disease using analytes prepared from body fluid of a patient as a marker. As the substrate, common glass plates may be used and for example, avidin is used to attach desired proteins to a glass plate. Alternatively, polystyrene may be used as substrate material. The polystyrene substrate has an advantage that proteins can be readily attached with high attachment efficiency. In addition, a polyvinyl chloride or polypropylene substrate can be used according to natures of proteins to be attached to the substrate.

Processes for integrating proteins on the above-described substrates are well known to those skilled in the art. For example, when using a polystyrene substrate, 8 grooves a width of 1 mm, a length of 2 mm and a depth of 1.5 mm are formed at intervals of 1 mm on a 1.5 cm×1.5 cm polystyrene substrate. Proteins to be analyzed are deposited as agglomerates spaced from each other with a predetermined distance in each groove. For instance, where proteins are deposited as agglomerates with a diameter of 400 nm at intervals of 500 nm, 10 different proteins can be deposited over a length of 1 cm. That is, 80 different proteins can be deposited in a substrate.

As fluorescent material which can label an analyte in a liquid sample in the laser-induced epifluorescence detecting method and apparatus according to the present invention, fluorescent materials having a difference of 20 nm or more between its absorption wavelength and emission wavelength may be used. Representative examples of such fluorescent materials include, but are not limited to, fluorescent particles, quantum dots, lanthanide chelates, such as samarium (Sm), Europium (Eu) and Terbium (Tb), and fluors, such as FITC, Rhodamine green, thiadicarbocyanine, Cy2, Cy3, Cy5, Cy5.5, Alexa 488, Alexa 546, Alexa 594 and Alexa 647). Preferred fluorescent materials which can be used in detection of DNA are Cy3 and Cy5. In general, the fluorescence intensity is directly proportional to the intensity of excitation light.

The lasers which can be used in the laser-induced epifluorescence detecting method and apparatus according to the present invention include He—Ne lasers and diode lasers. Examples of the He—Ne lasers may include an accurate and downsized portable iodine-stabilized He—Ne laser developed in cooperation with the National Research Laboratory of Metrology (NRLM), Agency of Industrial Science and Technology (AIST), ministry of International Trade and Industry (MITI) and model 05 LYR 173, produced by Melles Griot (Irvine, Calif.). The diode-laser is more accurate and compact than the He—Ne laser and includes infrared and red diode lasers.

The laser-induced epifluorescence detecting apparatus used in the present invention comprises a laser, an exciter filter, an elliptical reflecting mirror or spherical mirror, epifluorescence sample control means, a collimator, a fluorescent filter and an optical detector, as described above. Now, the principle of collecting epifluorescence by such construction will be explained referring to FIG. 12 and FIG. 13 while comparing with the conventional epifluorescence detecting apparatus.

Figure 12:
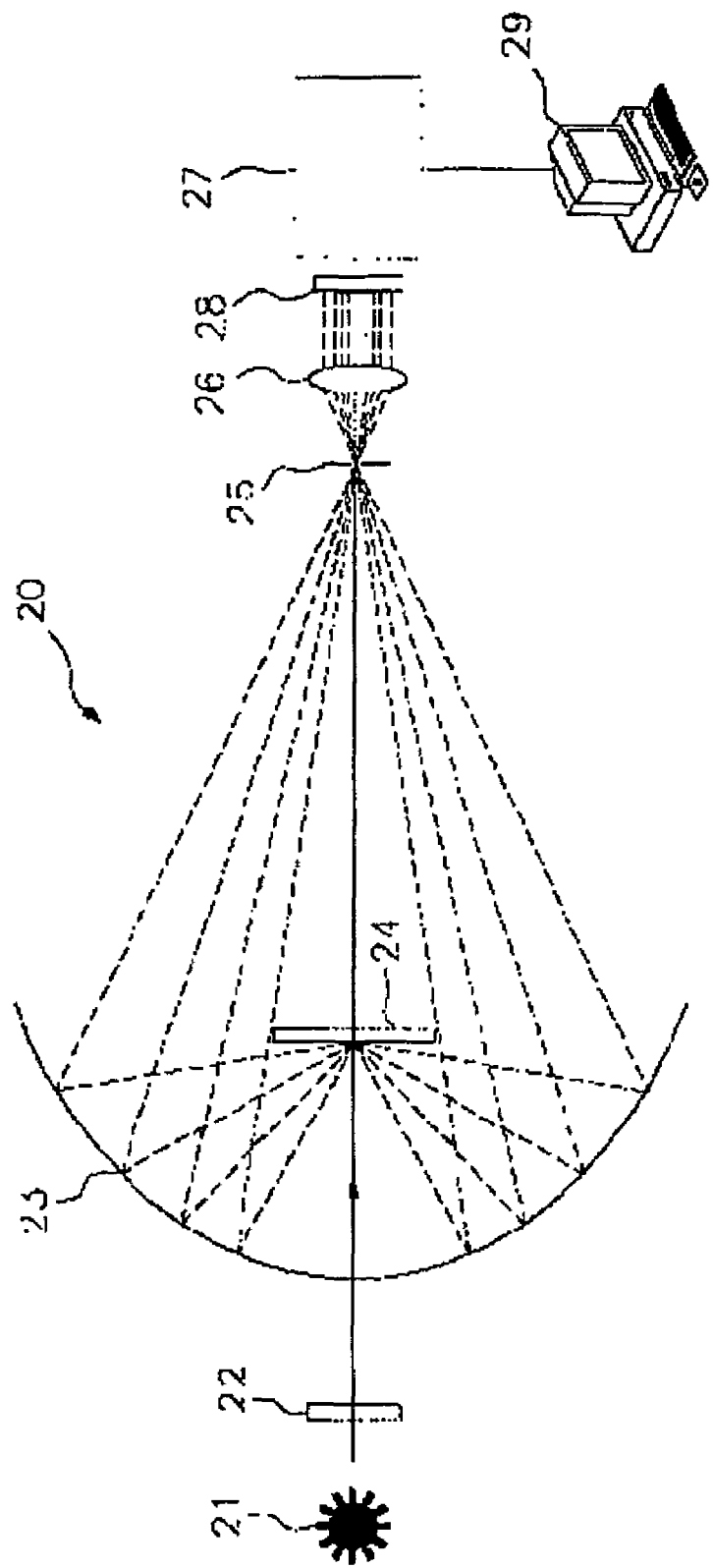
FIG. 12 is a view illustrating a structure of a laser-induced epifluorescence detecting apparatus with an elliptical reflecting mirror according to the present invention.

FIG. 12 shows a laser-induced epifluorescence detecting apparatus with an elliptical reflecting mirror, in which incident light is focused upon the first point of the elliptical reflecting mirror where the sample is disposed and the light focused upon the second point of the elliptical reflecting mirror is converted into parallel light to detect the epifluorescence. The laser can emit light at a wavelength corresponding to the maximum excitation band of a certain fluorophore. In one embodiment, the laser 21 is a 2 mW He—Ne laser emitting light at a wavelength of 594 nm which is approximate to the maximum absorption of Alexa, a fluorescence-labeling substance. For example, a He—Ne laser model 05 LYR 173 (Melles Griot, Irvine Calif.) may be used. Light from the laser 21 passes through the incident filter (exciter filter) 22 and then a hole disposed at the middle point between the incident filter 22 and an elliptical reflecting mirror 23. Here, the elliptical reflecting mirror 23 is preferably aligned in a straight line with the incident filter 22 so that the light from the laser can properly pass through the incident filter 22 and then the elliptical reflecting mirror. After passing through the elliptical reflecting mirror, the light is focused to the surface of the sample (DNA chip or protein chip) fixed on the sample control means 24. The sample may be moved upward and downward or back and forth to a proper position so that the light can be optimally focused to the surface of the sample. The focal point is located at the first point of the elliptical reflecting mirror 23. The fluorescence emitted from the sample positioned at the first focal point of the elliptical reflecting mirror and scattered light of the incident light are reflected by the elliptical reflecting mirror 23 and focused to the spatial filter 25 at its second focal point. The spatial filter serves to remove noise created by dust, etc. on the surface of the sample. After passing the spatial filter, the light is converted into parallel light by the collimator 26. The parallel light is filtered again through the fluorescent filter 28 to remove the scattered light and subsequently, pure fluorescence components enter the optical detector 27. In the optical detector 27, the fluorescence components are converted into signals expressing their fluorescence intensities, which are transmitted to a computer 29, in which they are processed.

Figure 13:
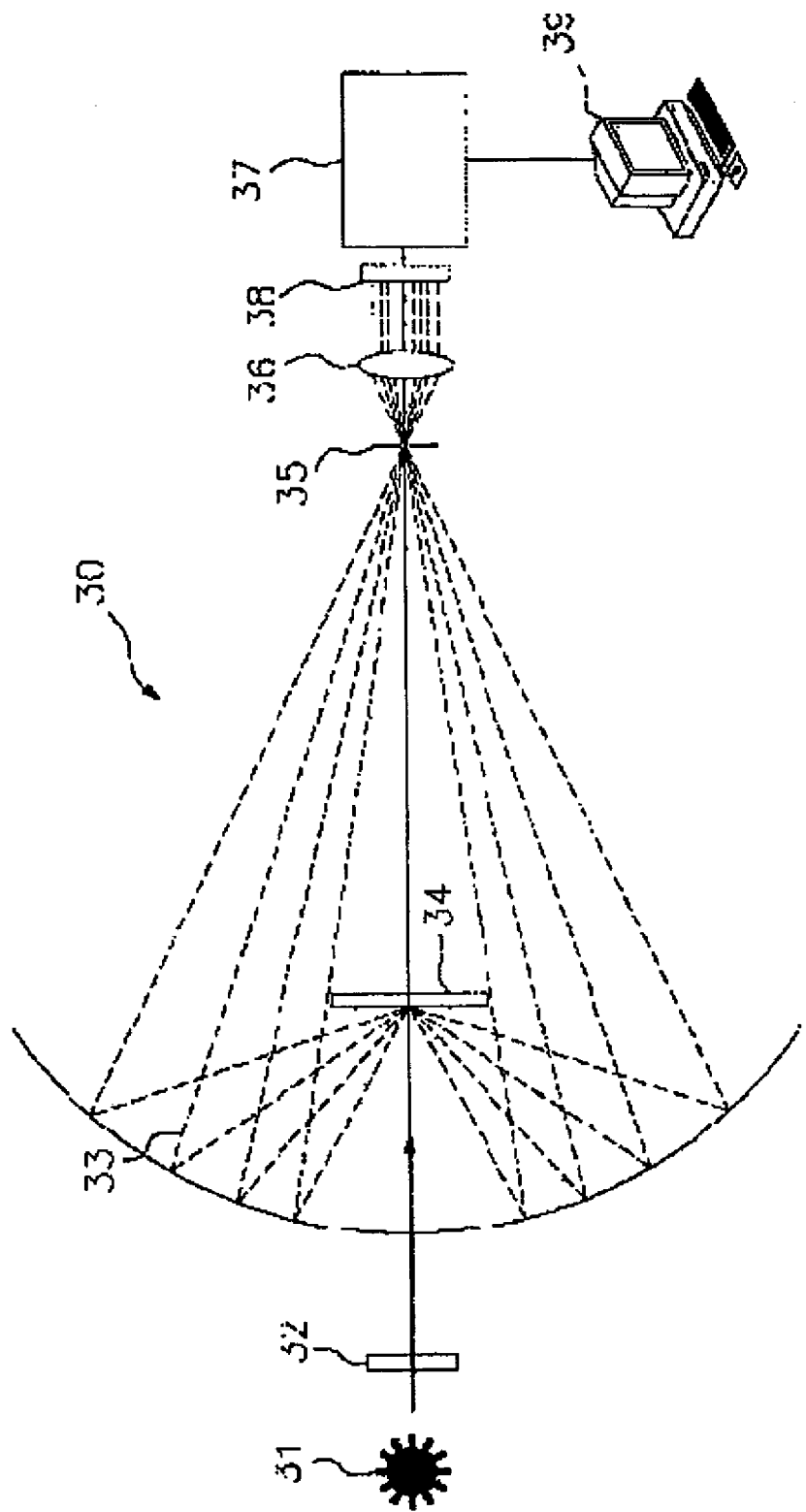
FIG. 13 is a view illustrating a structure of a laser-induced epifluorescence detecting apparatus with a spherical reflecting mirror according to the present invention.

FIG. 13 shows a laser-induced epifluorescence detecting apparatus according to the present invention with an spherical reflecting mirror, instead of the elliptical reflecting mirror as shown in FIG. 2, in which fluorescence of the sample obtained by focusing incident light to the surface of the sample is focused to the image point of the spherical mirror and the light is converted into parallel light for detection of the epifluorescence. The procedure for detecting epifluorescence of the sample using the apparatus of FIG. 13 is the same as described for the apparatus of FIG. 12. Light from the laser 31 passes through the incident filter (exciter filter) 32 and then a hole disposed at the middle point between the incident filter 32 and a sample control means 34. Here, the spherical reflecting mirror 33 is preferably aligned in a straight line with the incident filter 32 so that the light from the laser can properly pass through the incident filter 32. After passing through the spherical mirror, the light is focused to the surface of the sample fixed on the sample control means 34. The sample may be moved upward and downward or back and forth to a proper position so that the light can be optimally focused to the surface of the sample. The focal point is located at the first point of the spherical mirror 23. The fluorescence emitted from the spherical mirror and scattered light of the incident light are reflected by the elliptical mirror 33 and focused to the spatial filter 35 at its second focal point. The spatial filter serves to remove noise created by dusts, etc. on the surface of the sample. After passing the spatial filter, the light is converted into parallel light by the collimator 36. The parallel light is filtered again through the fluorescent filter 38 to remove the scattered light and subsequently, pure fluorescence components enter the optical detector 37. In the optical detector 37, the fluorescence components are converted into signals expressing their fluorescence intensities, which are transmitted to a computer 39, in which they are processed.

Figure 21:
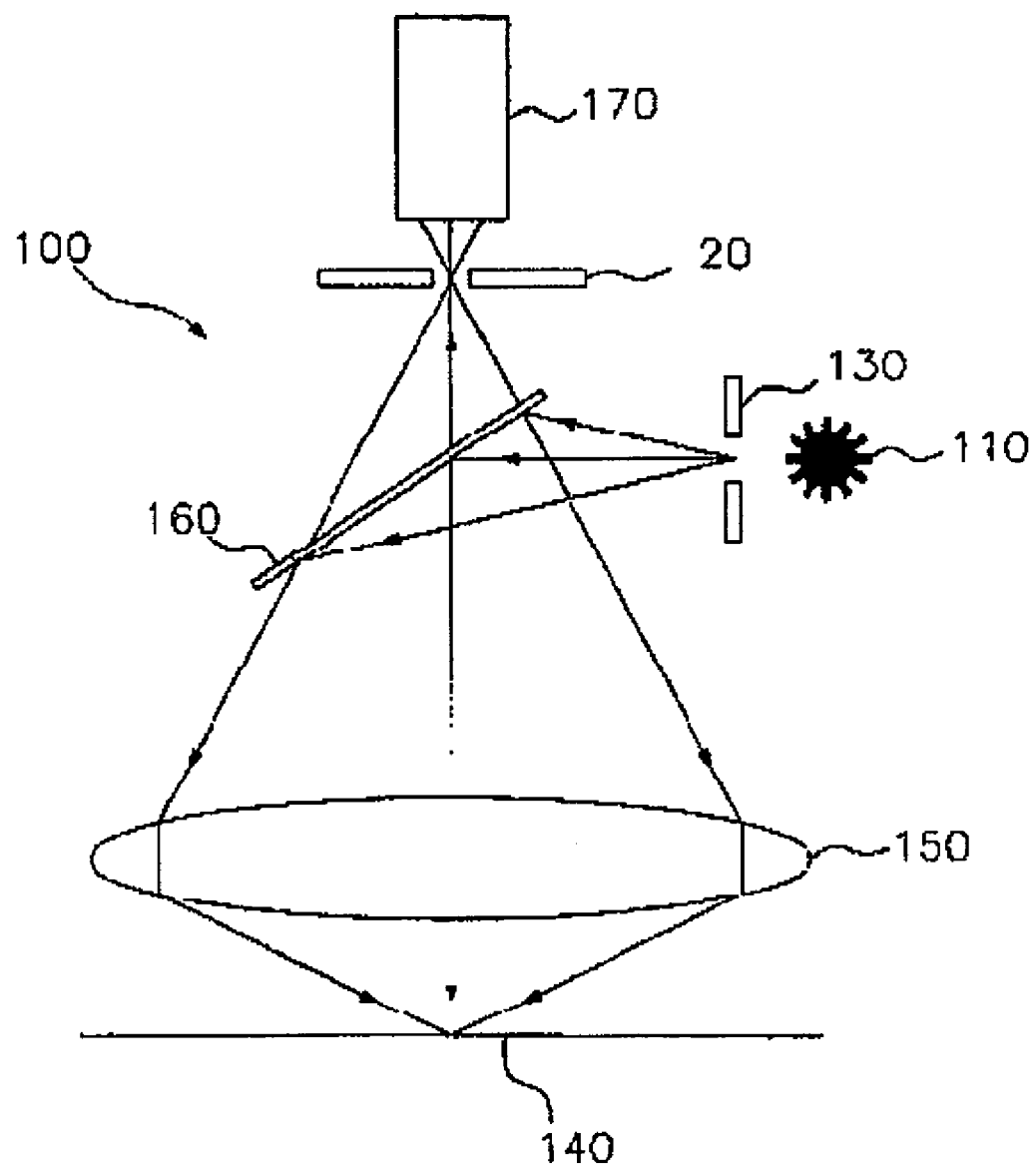
FIG. 21 is a view illustrating a structure of a conventional laser-induced epifluorescence detector.

Meanwhile, according to the conventional epifluorescence detecting apparatus as shown in FIG. 21, light from a laser passes through an aperture 130 and then is reflected by a beam splitter 160. The reflected light passes through a lens 150 and then is focused to the surface of the sample. The fluorescence emitted from the surface of the sample 140 passes again through the lens 150 and to be focused to an aperture 120 before entering a detecting apparatus 170. In this case, since the area in front of the sample 140 is exposed to the outside, a great quantity of the fluorescence emitted from the surface can be scattered to the air to be lost, not passing through the lens. As contrast, in the detecting apparatuses according to the present invention, epifluorescent samples 24, 34 are located in the concave region of the elliptical reflecting mirror 23 or spherical mirror 33. Therefore, the great majority of fluorescence from the samples can be reflected by the elliptical reflecting mirror 23 or spherical mirror 33, not being scattered to the air and thereby, there is little chance for fluorescence to be lost. Moreover, in the epifluorescence detecting apparatus according to the present invention, since the collimator 26, 36 is used to convert the fluorescence reflected by the elliptical reflecting mirror or spherical mirror 33 into parallel light, there is little chance for signal to be lost on the way to the optical detector 27, 37.

In sum, the laser-induced epifluorescence detecting apparatus according to the present invention employs a reflective surface which surrounds the sample, instead of a lens, to focus the epifluorescence, and consequently, 97% or more of the emitted epifluorescence can be reflected by the reflective surface toward the optical detector (excluding the loss due to the hole through which the incident light enters). The sample and the sample control means shield a part of the reflected epifluorescence, but the remaining epifluorescence with the exception of such inevitable losses due to the structure of the apparatus all reaches the optical system. When the diameter of the reflecting mirror is 10 cm and the size of the sample control means is 2×10 cm, the loss due to blocking by the sample control means is on the order of about 20%, which includes the loss by the hole for entry of incident light. Therefore, according to the present invention, it can be expected that the fluorescence collecting efficiency is raised to 80% or more over 10% of the conventional lens type fluorescence collecting device.

Figure 23:
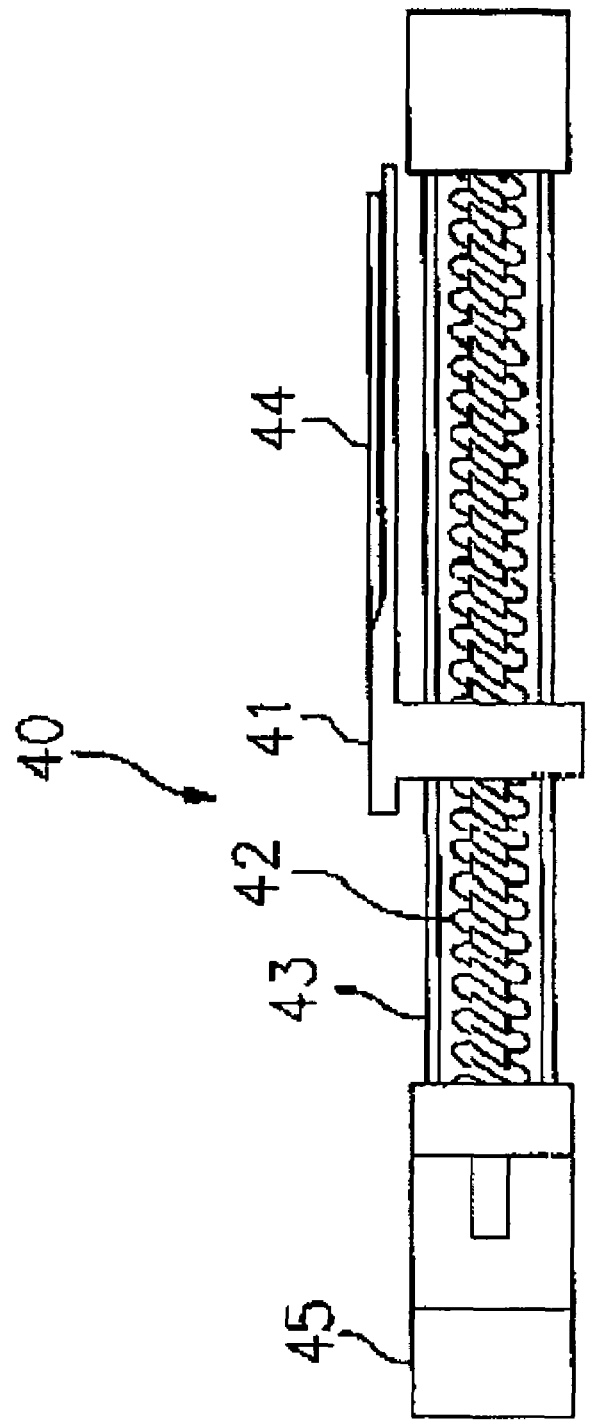
FIG. 23 is a view illustrating a structure of a sample controller, a component of the laser-induced epifluorescence detecting apparatus according to the present invention.
Figure 24:
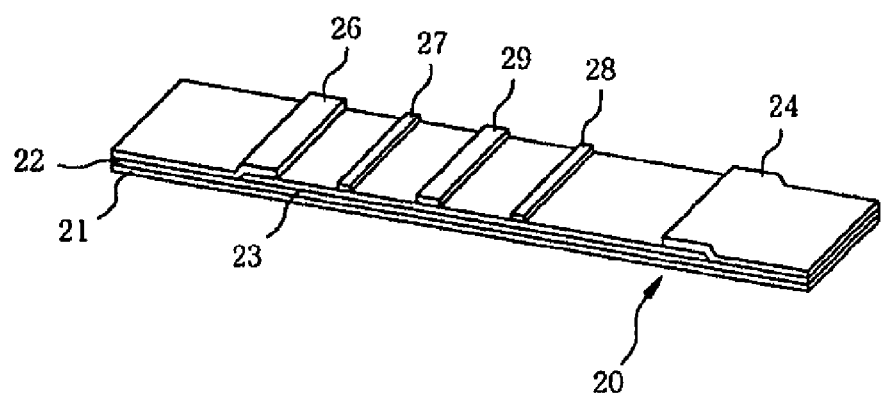
FIG. 24 is a perspective view of another embodiment of a lateral flow quantitative assay strip, note that there is no releasing pad (3) in this embodiment that is present in FIG. 2.
Figure 25:
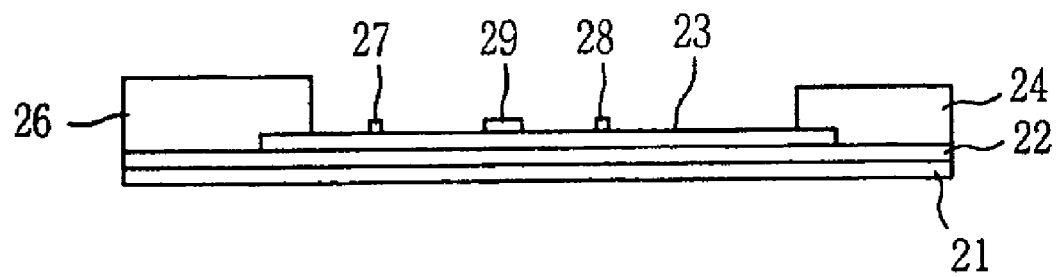
FIG. 25 is a side view of the lateral flow quantitative assay strip of the embodiment shown in FIG. 24.

FIG. 23 is a view illustrating a structure of a sample control means in an embodiment of the present invention. In FIG. 23, the holder 41 consists of the upper part into which one end of a sample (mounted on strip or chip) is inserted and fixed and the lower part connects with a pitch wheel of a moving means 42 so that the sample can move in front and rear directions of the pitch wheel. As the moving means 42 spins by a motor 45, it can move in front and rear directions to keep up with a guide 43 equipped side by side by the moving means 42.

In general, cut-offs of analytes to be analyzed in blood are described in Table 2 (microcystin is an environmental material, existing in water but not in blood).

TABLE 2

| Marker | Unit | Cut-off |
|---|---|---|
| CEA | ng/ml | <5 |
| AFP | ng/ml | <15 |
| PSA | ng/ml | <4 |
| B2M | ng/ml | <2 |
| NSE | ng/ml | <15 |
| CYFRA21-1 | ng/ml | <3.5 |
| Myoglobin | ng/ml | <70 |
| CK-MB | ng/ml | <3 |
| CtnI | ng/ml | <1 |
| CTnT | pg/ml | <60 |
| BNP | pg/ml | <100 |
| Microcystin | pg/ml | <300 |

In an additional embodiment according to the present invention, analytes which can be analyzed at a level of pg/ml include those described in Table 3, but are not limited thereto.

| Analytes | Unit | Cut-off |
|---|---|---|
| ACTH | pg/ml | 200-250 |
| Adrenomedullin | pg/ml | 480 ± 135 |
| ANP | pg/ml | 73 |
| Angiotensin II | pg/ml | 21 ± 4 |

-continued

| Analytes | Unit | Cut-off |
|---|---|---|
| Calcitonin | pg/ml | 10 |
| CNP | pg/ml | 7.36 ± 3.0 |
| Endorphin | pg/ml | 30 ± 5 |
| Gastrin | pg/ml | 26.4 ± 8.4 |
| Ghrelin | pg/ml | 87.79 ± 10.27 |
| NPY | pg/ml | 70.7 ± 5.9 |
| Pancreatic polypeptide | pg/ml | 218 ± 23 |
| Urotensin | pg/ml | 7.70 ± 0.97 |

It has been found that the laser-induced epifluorescence detecting apparatus according to the present invention can assay analytes to a pg/ml level.

Now, the present invention will be described in detail using an embodiment shown in the following examples. However, the examples are for illustration of the present invention and do not limit the scope of the present invention thereto.

EXAMPLE 1

Preparation of Monoclonal Antibody for Use as Detector and Captor (1) Preparation of Culture Medium Powdered Dulbecco's modified Eagle's media (DMEM) was dissolved in 900 ml of DDW and 3.7 g of sodium bicarbonate was added to the solution to adjust pH to 6.9. The solution was sterilized using a filter having a pore size of 0.45 μm, thus obtaining "incomplete DMEM". 450 ml of the incomplete DMEM was supplemented with 10% bovine calf serum and antibiotic penicillin-streptomycin to obtain "complete DMEM". 5 ml of the complete DMEM was mixed with 5 ml of 100×HT to form HT (hypoxanthine+thymidine) and 5 ml of 100X HAT (hypoxanthine+aminopterin+thymidine) to form a HT medium and HAT medium, respectively.

(2) Preparation and Injection of Antigen

For the first injection, purified enzyme protein solution (50 μg) was mixed with an equal volume (typically 0.3 ml) of complete Freund's adjuvant and the mixture was subjected to sonication for 30 seconds. The resulting solution was injected to BALB/c mice at a dose of 0.4 ml. Three weeks after the first injection, the additional injection was performed to the mice using a solution prepared by mixing the protein solution used for the first injection with incomplete Freund's adjuvant. This booster injection was repeated 2 or 3 times. The final injection was performed using only the protein without any adjuvant 3 to 4 days before a cell fusion experiment. The mice used in the experiment were 6 to 8 weeks old BALB/c, without distinction of sex.

(3) Preparation of Feeder Cells

The feeder cells were prepared 1 to 2 days before the fusion experiment. A mouse, at least 10 weeks old, was sacrificed and the abdominal skin was removed with great care. 5 ml of 11.6% sugar solution was injected intraperitoneally. 1 or 2 minutes later, the injected sugar solution was recovered in an amount of at least 3 ml. The solution was centrifuged (2,000 rpm, 3 minutes) to obtain feeder cells. The feeder cells were suspended in 30 ml of HAT medium and the resulting solution was placed in five 96-well plates, one drop for each well. When the mouse was small, two mice were used to obtain abdominal cells. Also, when contaminating red blood cells were present, the preparation was repeated.

(4) Preparation of Spleen Cells

A mouse immunized with an antigen was sacrificed and its spleen was removed under sterile conditions. The spleen was transferred to a culture dish to which 10 ml of incomplete DMEM had been added in advance and its tissue was disrupted with tweezers, upon which the spleen cells were released to the culture medium. The cells were moved to a 15 ml tube to settle any large or uncrushed tissues for 2 minutes. A 5 ml aliquot from the upper part was centrifuged. The supernatant was removed and the cells were dissolved into 3 ml of incomplete DMEM, which was to be mixed with myeloma cells. For one cell fusion experiment, $3\times10^7$ spleen cells were prepared.

(5) Preparation of Myeloma Cells

At 5 days before the cell fusion experiment, SP2/0 Ag14 cells in frozen state were taken out of a liquid nitrogen tank and thawed. The cells were recovered while very slowly adding complete DMEM. Centrifugation was performed to settle the cells, which were resuspended in 10 ml of complete DMEM and passaged at intervals of two days in a $CO_2$ incubator at 37° C. $5\times10^7$ myeloma cells were prepared for the cell fusion experiment.

(6) Cell Fusion

The prepared spleen cells and myeloma cells were mixed and centrifuged (2,000 rpm, 3 minutes). The cells were washed once with 20 ml of incomplete DMEM and the supernatant was thoroughly removed. Cell fusion was carried out by grasping the cell vial with hands to maintain a temperature of 37° C. while tapping the lower part of the tube to disrupt the cells. 1 ml of 50% PEG (polyethyleneglycol) solution was added dropwise to the tube over 1 minute and the tube was shaken for 90 seconds to effect the cell fusion. Exactly 2 minutes and 30 seconds after adding the first drop of PEG solution, incomplete DMEM was added to stop the reaction. Here, in order to protect membranes from damage caused by the osmotic pressure shock upon addition of the PEG solution, the addition of incomplete DMEM was carried out by first adding 1 ml over 1 minute, then 2 ml over 1 minute, then 3 ml over 1 minute and so on, until a total 20 ml of incomplete DMEM had been added to the tube. The Cells thus fused were centrifuged and washed with 20 ml of HAT medium to thoroughly remove PEG. The resulting cells were suspended in 20 ml of HAT medium and the resulting solution was added to the 96-well plates, two drops for each well, and cultured in a $CO_2$ incubator at 37° C.

On the third day after the cell fusion, three drops of HT medium were added to each well. The medium of each well was changed at intervals of 3 days and the growth of cells were examined under a microscope. Typically, hybridoma colonies first appeared four days after the fusion and screening of the colonies commenced about 7 days after the fusion. 200 µl of the medium was transferred to a 24-well plate containing 400 µl of PBS. Cells of wells showing a positive ELISA response were transferred to a new 24-well plate containing 1 ml of HT medium and cultured for an additional 3 to 4 days. After completion of the culturing, 500 µl of the medium was added to a 15 ml tube containing 2 ml of PBS and subjected to a Western blot analysis. Again, cells showing a positive response were transferred to a 6-well plate containing 5 ml of HT medium and cultured. After culturing, the hybridoma cells were flash frozen and cloned by limiting dilution.

(7) Freezing of Hybridoma Cells

Confluent cells grown in a 10 ml culture flask were centrifuged. The settled cells were dissolved in 1 ml of a freezing media containing 90% bovine calf serum, 10% DMSO. The solution was put into a freezer vial, which was placed in a styrofoam box and slowly chilled to −70° c. After two hours, the vial was quickly transferred to a liquid nitrogen tank, in which the cells can be almost permanently preserved.

(8) Limiting Dilution of Hybridoma Cells

Limiting dilution was carried out to select cells capable of producing antibody against an epitope. Firstly, the number of hybridoma cells in log phase growth was calculated using a Neubauer Cell Counter and continuous dilution was performed until 15 cells were contained in 1 ml medium, that is, a drop of medium contained one cell. A drop of the medium was added to each well of the 96-well plate containing the feeder cells, which had been prepared one or two day(s) ago. Every 3 days, the medium was changed. At 5 days, the plate was scanned using an inverted microscope to mark wells where a single colony was observed. At 14 days, hybridoma cells of the marked wells were transferred to a 24-well plate and continuously cultured. After the cultivation, the media were tested by ELISA to identify hybridoma cells producing the desired antibody, which were then stored in a frozen state.

(9) Production of Ascites Fluid

When a large amount of monoclonal antibodies were needed, a BALB/c mouse which had been injected with 500 µl of pristine 9 days before was injected with about $1\times10^7$ of the hybridoma cells producing the desired antibody. 10 to 15 days later, the mouse showing proper abdominal distension was anesthetized or killed. Ascitic fluid was harvested using an syringe and centrifuged (15,000 rpm, 10 minutes) to remove cells and tissues. The supernatant was divided into portions, which were stored at −70° c. For subsequent experiments, IgG was isolated from the ascitic fluid kept in a frozen state using a Protein A column.

(10) Monoclonal antibodies for different analytes

|  | PSA | Free PSA | AFP | CEA |
|---|---|---|---|---|
| Antigen | Semen | Semen[a] | Amniotic fluid[b] | Human body fluid[c] |
| Captor antibody | 32c5 (IgG2a) | 83c1 (IgG1) | 5c3 (IgG2a) | 34 (IgG1) |
| Detector antibody | 1c1 (IgG2a) | 1c1 (IgG2a) | 20c4 (IgG1) | 17 (IgG2a) |
| Coating buffer solution | Phosphate buffer solution (0.1M, pH 7.4) | Tris buffer solution (0.15M, pH 8.0) | Borax buffer solution (0.2M, pH 8.3) | Carbonate buffer solution (0.5M, pH 9.5) |
| Labeling buffer solution | PBS | PBS | PBS | PBS |

[a]Obtained from Scripps;
[b]Obtained from RDI;
[c]Obtained from Biodesign

EXAMPLE 2

Preparation of Protein-Fluorescent Material Conjugate

A fluorescent material as a signal generating source was ligated to the mouse monoclonal antibody against an analyte of interest for use in subsequent experiments. Proteins to be used in binding of the fluorescent material were purified to a purity of at least 95%. The proteins were used at a concentration of at least 1 mg/ml for optimal binding. The purified proteins were dialyzed against a buffer solution (0.1 M sodium bicarbonate, pH 8.5) not containing ammonia or amine ions in a refrigerator at 4° C. for 12 to 24 hours in order to facilitate the reaction with the fluorescent material. The proteins dialyzed were kept in a refrigerator or −20° C. freezer until use. The proteins dialyzed in the buffer solution were directly but slowly added to powdered Alexa 647 (Molecular Probes, USA) and the reaction was stirred for 1 to 2 hours in a refrigerator at 4° C.

EXAMPLE 3

Purification of Protein-Fluorescent Material Conjugate

Excess unreacted fluorescent material was removed using a distribution column packed with Sephadex G-25. As a purifying buffer solution, 0.1 M sodium carbonate (pH 8.5) was used. The purified protein-fluorescent material conjugates were kept in a refrigerator or −20° C. freezer until use.

EXAMPLE 4

Immobilization of Protein on Nitrocellulose Membrane

The proteins were immobilized on a nitrocellulose membrane in a thin line shape with varying the concentration and amount of protein. The membrane with immobilized proteins was stored in a dehumidifier kept at 25° C. and a humidity of 35 to 50% for 2 hours. Then, in order to stabilize the protein and prevent non-specific reactions between reagents, the membrane was treated with a stabilizing solution (1% BSA, 0.05% Tween 20, 1% sucrose, 0.1% PVA) and equilibrated for 5 minutes. As the components of the stabilizing solution, BSA may be substituted with gelatin, Tween 20 may be substituted with Triton X-100, sucrose may be substituted with trehalose, PVA (polyvinylalcohol) may be substituted with PEG or PVP (polyvinylpyrrolidone). After removing excess solution the membrane was dried at 40° C. for 30 minutes. The dry membrane was stored in an appropriate container kept at 25° C. and a humidity of 35 to 50% until use.

EXAMPLE 5

Pretreatment of Sample Pad

The sample pad was pretreated in order to facilitate movement of components of a solution through the nitrocellulose membrane, to maintain a high sensitivity of reaction and to prevent experimental errors due to a non-specific reaction between protein-fluorescent material polymer and a sample.

A sample pad (2.5×30 cm) was sufficiently wetted with a pretreating solution (20 mM Tris-Cl, 0.1% Triton X-100, 0.05% NaN$_3$, pH 8.5) by repeatedly applying 1 ml of the solution and equilibrating for 10 minutes. When whole blood was used as a sample, another pretreating solution (PBS, 10 mM phosphate, 150 mM NaCl, 1% BSA, 0.05% Tween 20, 0.05% NaN$_3$, pH 7.4) was used to prevent hemolysis of red blood cells. After removing excess solution, the sample pad was vacuum dried at a temperature of 50☐ to 60☐ for 1 hour to prevent deformation of the pad. The lyophilization method was selected to minimize denaturation of the protein-fluorescent material conjugate. The prepared sample was stored in an appropriate container under the same conditions as for the foregoing membrane.

EXAMPLE 6

Preparation of Conjugate Releasing Pad

The protein-fluorescent material conjugates as a detector for an analyte of interest were immobilized upon a pad made of glass fiber, thereby simplifying the assay procedure to a one step process.

The protein-fluorescent material conjugates were diluted 1/1000, 1/500, 1/100 in a buffer solution (PBS, 0.1% gelatin, 0.1% Tween 20, pH 7.4). The general method for applying the mixture to the pad includes soaking a glass fiber pad with the mixture and equilibrating for 5 minutes at room temperature, followed by drying. However, in this example, the mixture was dispensed in an amount of 10, 15, 20 µl/cm using a micro dispenser in order to prevent nonuniform redistribution of the mixture on the surface of the glass fiber pad and to reduce a needed amount of the mixture. The conjugate releasing pad (protein-fluorescent material conjugate pad) can be dried by three methods. The first method was to dry the pad at a temperature below 40° C. for 6 hours, considering stability of the protein component. The second method was to dry the pad in a dehumidifier at room temperature for 16 hours. As the third method, lyophilization may be selected to reduce any chance of the protein component being inactivated, though this method requires more time than the first method. The prepared conjugate releasing pad was stored in an appropriate container under the same conditions as for the foregoing membrane.

EXAMPLE 7

Dispensation of Protein on NC (Nitrocellulose) Membrane

Each protein to be immobilized on the membrane was diluted in PBS buffer solution to 1 and 2 mg/ml. The solution was dispensed in an amount of 0.88 µl/cm in a line with a width of 0.8 mm on the NC membrane using the Bio Dot dispenser and fixed at RH 35 to 50% for 2 hours. Then, the membrane was treated with a stabilizing solution (1% BSA, 0.05% Tween 20, 0.1% PVA) for stabilization of proteins and prevention of non-specific reactions between reagents, and equilibrated for 5 minutes (As the components of the stabilizing solution, BSA may be substituted with gelatin, Tween 20 may be substituted with Triton X-100, sucrose may be substituted with trehalose, PVA (polyvinylalcohol) may be substituted with PEG or PVP (polyvinylpyrrolidone)). After removing excess solution, the treated membrane was dried at 40° C. for 30 minutes. The resulting dry membrane was assembled with the sample pad, absorption pad, etc. and cut to a width of 4 mm using a cutter so that the final strip had a dimension of 4×60 mm.

EXAMPLE 8

Quantification of Analyte (Single Test Line)

The captor antibody (1 mg/ml) against PSA (prostate specific antigen) to be analyzed was dispensed in the test line region on the NC membrane in an amount of 0.88 µl/cm and rabbit IgG (1 mg/ml, 0.1 mg/ml, 0.05 mg/ml 0.01 mg/ml) was dispensed on the reference line in an amount of 0.88 µl/cm.

The resulting membrane was stored at RH of 35 to 50% for 2 hours for immobilization. Then, the membrane was treated with a stabilizing solution (1% BSA, 0.05% Tween 20, 0.1% PVA) for stabilization of proteins and prevention of non-specific reactions between reagents, and equilibrated for 5 minutes. After removing excess solution, the treated membrane was dried at 40° C. for 30 minutes. The material to react with the protein to be analyzed via antigen-antibody reaction was fluorescently-labeled with Alexa 647. Also, the antibody (antigen ?) to bind to the protein dispensed on the reference line via antigen-antibody reaction was fluorescently-labeled with Alexa 647. The protein-fluorescent material conjugates were diluted 1/100 in a dilution buffer solution (PBS, 0.1% gelatin, 0.1% Tween 20, pH 7.4). 5% trehalose as a stabilizing agent was added to the diluted solution. The solution was then dispensed in an amount of 20 µl/cm on the surface of glass fiber using a dispenser, followed by lyophilizing.

The prepared NC membrane, conjugate releasing pad, sample pad and absorption pad were adhered to the backing and assembled in a plastic housing. The PSA standard solution was diluted in a dilution buffer solution (PBST, 10 mM phosphate, 150 mM NaCl, 0.3% Tween 20, pH 7.4) to 0, 4, 8, 16 and 32 ng/ml. The concentrations of the prepared standard solutions were confirmed using a PSA ELISA kit. For proteins dispensed on the reference line, each standard solution as prepared above was dropped in a specimen input hole of the assay kit and 10 minutes later, the kit was placed in the laser-induced epifluorescence detecting apparatus according to the present invention. The apparatus is designed to express an amount of fluorescence of the detector/analyte/captor conjugates accumulated on a test line or reference line as a peak and display the amount on a monitor. The amount of the Rabbit IgG showing a peak similar to 8 ng/ml PSA was determined as the amount to be dispensed on the reference line. After determining the concentration of the reference line, respective PSA standard solutions were applied to the assay kits while following the same method as described above. 10 minutes later, the apparatus displayed the numerical value of fluorescence intensity of the analyte which was calculated by inputting a ratio of the fluorescence intensities of the test line and the reference line into an analogized equation by the polynomial regression method, to obtain the numerical value of the fluorescence intensity of the analyte.

EXAMPLE 9

Quantitative Analysis of Total/Free PSA

Figure 19:
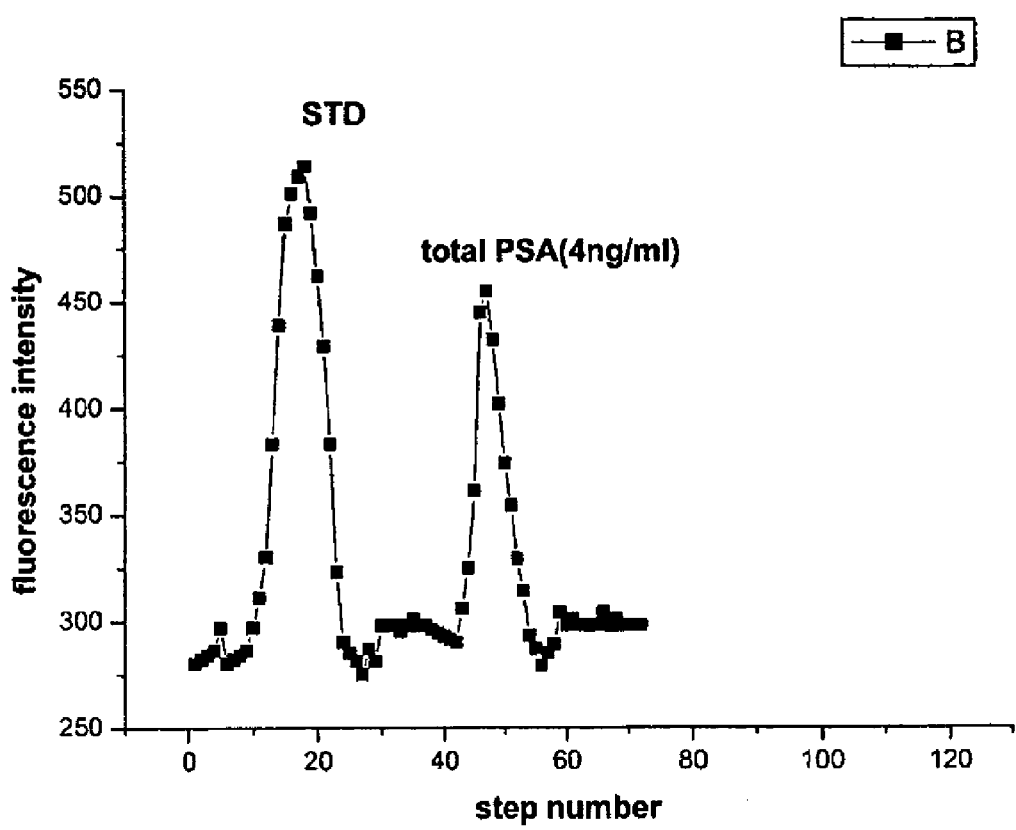
FIG. 19 is a graph showing the result of measuring the fluorescence intensity of the total PSA using the laser-induced epifluorescence detecting apparatus according to the present invention.
Figure 20:
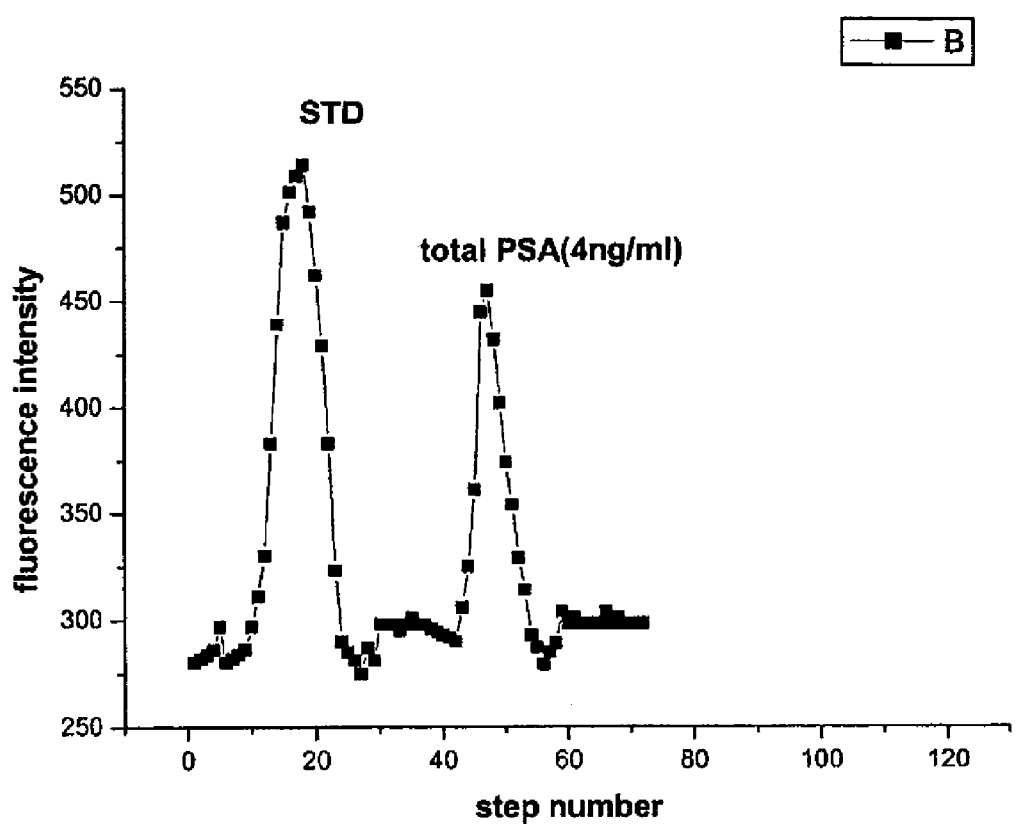
FIG. 20 is a graph showing the result of measuring the fluorescence intensity of the free PSA using the laser-induced epifluorescence detecting apparatus according to the present invention.

A monoclonal antibody (1 mg/ml) specifically reacting with total PSA and free PSA were dispensed on the NC membrane in an amount of 0.88 µl/cm. Separately, a monoclonal antibody having an epitope different from that of the capture antibody was bound to a fluorescent material, Alexa 647, to form an antibody/fluorescent material conjugate. This conjugate was mixed with a PBS buffer solution containing 5% trehalose, 1% gelatine as a stabilizer to obtain a 1/100 dilution. A glass fiber pad was impregnated with the dilution in an amount of 50 µl/cm², and lyophilized to obtain an antibody/fluorescent material conjugate pad. The antibody/fluorescent material conjugate was dissolved in a PBS buffer solution containing 1% of gelatin in the dilution ratio of 1/1000, to make the buffer solution of the antibody/fluorescent material conjugate. The PSA standard solution was diluted with a dilution buffer solution (PBST, 10 mM phosphate, 150 mM NaCl, 0.3% Tween 20, pH 7.4) to 0, 4, 8, 16 and 32 ng/ml. The concentrations of the prepared standard solutions were confirmed using a PSA ELISA kit. Each standard solution as prepared above was dropped in a specimen input hole of the assay kit and 15 minutes later, each test zone (two zones for total PSA and free PSA) was examined for fluorescence intensity using the laser-induced epifluorescence detecting apparatus according to the present invention. In case of an actual specimen such as serum or whole blood, a concentration of the specimen was determined using a PSA ELISA kit before the specimen was applied to the assay strip. The results are shown in FIG. 19 and FIG. 20.

EXAMPLE 9.1

Comparative Test of the Conjugate Pad and the Conjugate Solution

A reproducibility was compared between the detector in a solution and the detector attached to a releasing pad as one of strip components. The test was repeated ten times with the PSA samples of 1, 4, 10, 25, and 50 ng/ml respectively, and the average values and CV values were calculated. As shown in the results below, the reproducibility was much better for the detector in a solution rather than that attached to the releasing pad.

| Conc. Of PSA (ng/ml) | On the pad (%) | In the solution (%) |
| --- | --- | --- |
| 1 | 13.5 | 7.0 |
| 4 | 5.6 | 4.5 |
| 10 | 7.4 | 5.9 |
| 25 | 6.8 | 5.1 |
| 50 | 10.1 | 6.8 |

EXAMPLE 10

Quantitative Analysis of AFP, CEA, PSA, CRP (Multiple Test Lines)

Figure 16:
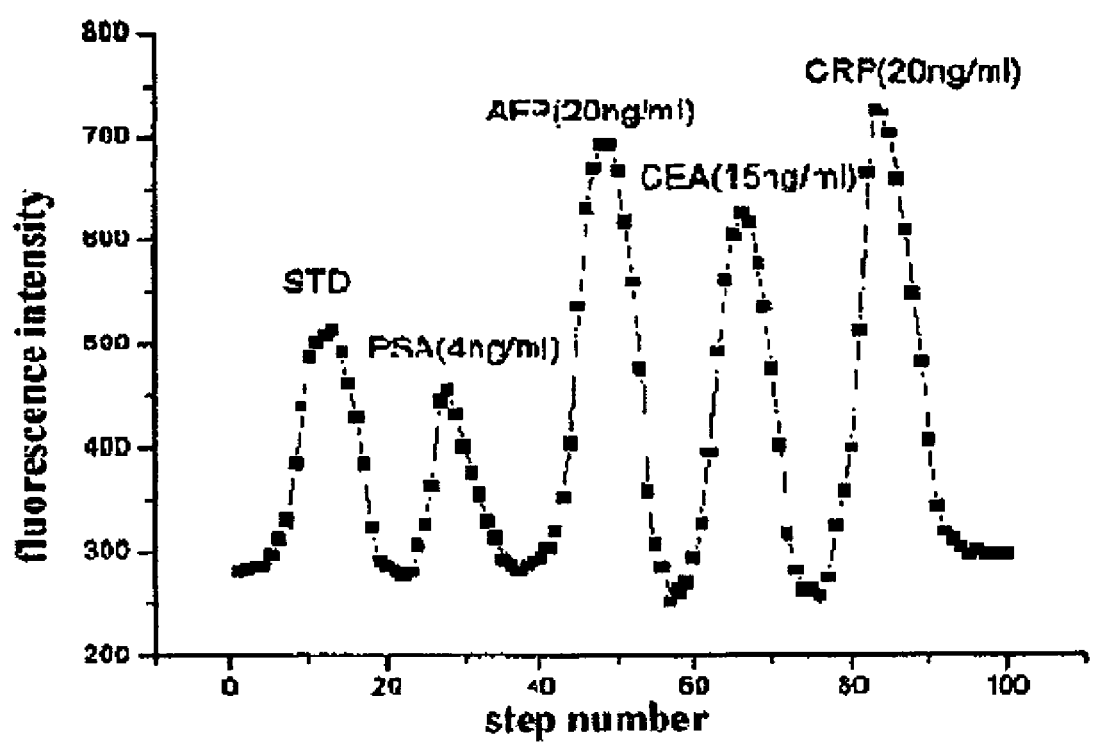
FIG. 16 is a graph showing results of quantification of a multi-test line strip using a laser-induced epifluorescence detecting apparatus with an elliptical reflecting mirror according to the present invention.

A pair of monoclonal antibodies specifically reacting with each of α-feto protein (AFP, a liver cancer marker), carcinoembryonic antigen (CEA, a tumor marker of many kinds of cancers, mainly used for colon cancer), catabolite regulatory protein (CRP) and PSA was prepared. The capture antibodies were dispensed sequentially in test lines at intervals of 2 mm from one end of the chromatography medium on the NC membrane in an amount of 0.88 µl/cm, one antibody for each test line. Two reference lines were dispensed at 2 mm in front of the first test line and at 2 mm in rear of the last test line, each line being 100 ul/ml. The NC membrane with the test and reference lines dispensed was fixed for 2 hours at RH 35 to 50%. Then, the membrane was treated with a stabilizing solution (1% BSA, 0.05% Tween 20, 0.1% PVA) for stabilization of proteins and prevention of non-specific reactions between reagents, and equilibrated for 5 minutes. After removing excess solution, the treated membrane was dried at 40° C. for 30 minutes. Other monoclonal antibodies having epitopes different from the immobilized antibodies were reacted with fluorescent material, to be used as detectors. Following the same method for quantitative analysis of total/free PSA, each conjugate of antibodies and fluorescent materials was diluted in a dilution buffer solution (5% trehalose, PBS containing 0.1% gelatin, pH 7.4) in ratio of 1/100, 11200, 1/150, and 1/100 for PSA, AFP, CEA and CRP, respectively. A glass fiber pad was impregnated with each solution in an amount of 50 µl/cm², followed by lyophilizing, to form a antibody/fluorescent conjugate pad. A specimen, of which concentrations had been confirmed using the ELISA kit, was mixed with a dilution buffer solution (10 mM phosphate, 150 mM NaCl, 0.3% Tween 20, pH 7.4) and the resulting dilution was applied to the test strip. 10 minutes later, intensities of fluorescences from the respective test lines were measured using the laser-induced epifluorescence detecting apparatus according to the present invention. The results are shown in FIG. 16.

EXAMPLE 11

Preparation of Fluorescently-Labeled Antigen or Antibody

Various types of fluorescent material were bound to antibodies and antigens for comparison. FITC (fluorescein-isothiocyanate), rhodamine, Alexa series, Cy3, Cy5 (Molecular probes, Inc.) were used as fluorescent materials in this examples. In the experiment, Alexa series, Cy3 and Cy5 showed excellent results in stability and reproducibility. In the subsequent experiments, Alexa 647 was used as a fluorescent material. The prepared fluorescent material/antigen (antibody) conjugate showed a stable reactivity and could be used for a sufficiently long period of time without decoloration.

EXAMPLE 12

Determination of Concentrations of Protein-Fluorescent Material Conjugate and Immobilized Protein on NC Membrane In order to determine optimum concentrations of a detector and a capture protein needed to detect an analyte, serial dilution was performed. Various amounts of a capture protein were immobilized on a NC membrane. Serial dilutions of a protein-fluorescent material conjugate were prepared. A standard solution of each analyte was mixed with the dilutions of the protein-fluorescent material conjugate and the mixture solution was applied to a test strip. After the development of the solution was completed, the test strip was assayed using the laser-induced epifluorescence detecting apparatus according to the present invention. The concentration of the immobilized protein was 1, 1.2, 1.4, 1.6, 1.8 and 2 mg/ml for each measurement item and the dispensed amount of the protein was 0.88 µl/cm. At a given concentration of the capture protein, when the concentration of the protein-fluorescent material conjugate was increased or decreased, the fluorescence intensity of the analyte at the same concentration was also increased or decreased. Additionally, at a given concentration of the protein-fluorescent material conjugate, when the concentration of the capture protein was changed, the same result as above was obtained. In both experiments, when the concentration exceeds a certain limit, non-specific reactions increased. By putting the above results together, the optimum concentrations of reagents which can lower the detection limit of an analyte and minimize non-specific reactions between the sample and the capture or the detector was determined.

EXAMPLE 13

Minimum Detection Limit of Analyte and Linearity

Figure 14:
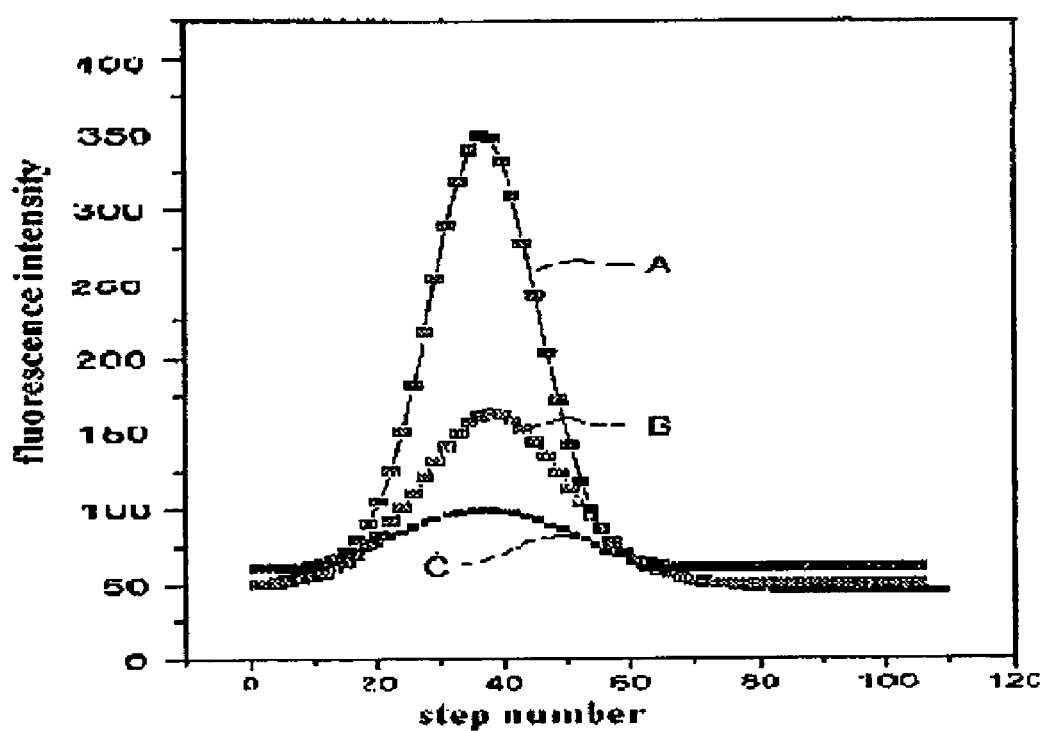
FIG. 14 is a graph showing the minimum detection limit concentration of a surface antigen of an analyte, as measured using a laser-induced epifluorescence detecting apparatus with an elliptical reflecting mirror according to the present invention (A: 4 ng/ml; B: 400 pg/ml; C: 40 pg/ml).

The PSA monoclonal antibody of the optimum concentration determined in Example 12 was dispensed at amount of 0.88 µl cm on a NC membrane. The antibody-fluorescent material conjugate diluted to the concentration determined in Example 12 was mixed with a dilution buffer solution (PBS containing 5% trehalose, 1% gelatine, pH 7.4). The resulting dilution was dispensed to a glass fiber pad in an amount of 20 µl/cm, followed by lyophilization, to obtain a antibody-fluorescent material conjugate pad. Then, the PSA standard solutions at a concentration in a range of 1 mg/ml to 1 pg/ml were applied to the strip to determine the minimum detection limit of the analyte and the linearity range of the assay kit using the epifluorescence analyser. As shown in FIG. 14, the minimum detection limit of PSA was 10 pg/ml and the linearity range was considerably wide, from 10 pg/ml to 1 µg/ml. AFP, CEA, CRP of Example 10 also showed minimum detection limits much lower than the cut-offs required for diagnosis.

EXAMPLE 14

In this example, for comparison, a fluorescence intensity of a fluorescent material was measured using the laser-induced epifluorescence detecting apparatus according to the present invention and a conventional laser-induced fluorescence detecting scanner, Scan Life, produced by GSI.

Figure 15:
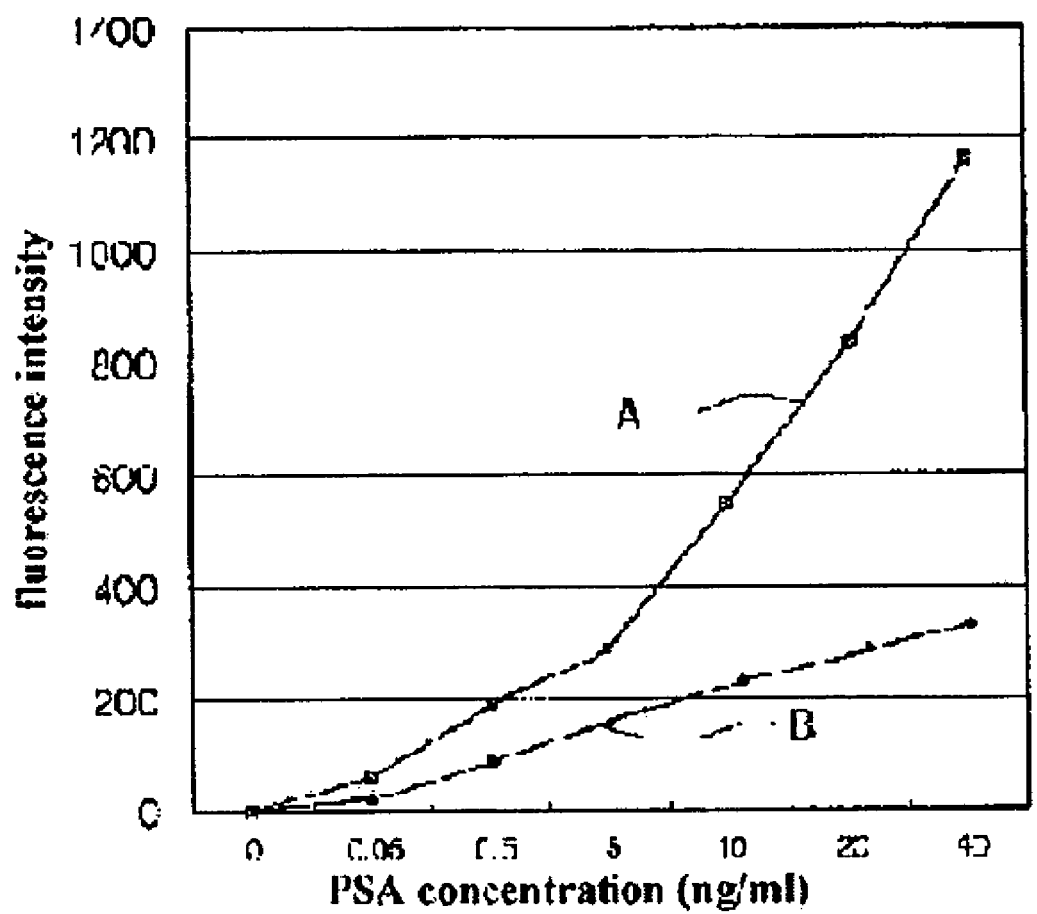
FIG. 15 is a graph showing epifluorescence intensities of PSA (Prostate Specific Antigen), as measured using a laser-induced epifluorescence detecting apparatus with an elliptical reflecting mirror (A) according to the present invention and a conventional fluorescence detecting scanner (B).

Serial dilutions of PSA as an analyte were prepared and mixed with the protein-fluorescent material. The mixture solution was applied to a strip as in Example 7. The result was imaged using the conventional scanner. Also, a lateral flow assay strip prepared using the same method and conditions was imaged using the laser-induced epifluorescence detecting apparatus according to the present invention. The imaged data were converted into numerical data using a related program. The results are shown in FIG. 15. From the results of FIG. 15, it was noted that both the laser-induced epifluorescence detecting apparatus according to the present invention and the conventional fluorescence detecting scanner showed a fluorescence intensity increasing according to the concentration of the analyte, while the fluorescence intensity measured by the laser-induced epifluorescence detecting apparatus according to the present invention was much higher than that measured by the conventional fluorescence detecting scanner.

EXAMPLE 15

Determination of Location of Reference Line

In order to determine the location of a reference line, three types of strips having a reference line in front of the test line, at the rear of the test line, and two reference lines at both locations, were prepared. For each type of strip, an analyte at different concentrations was assayed, each concentration being assayed 10 times. Thus, each of the analyte standard solutions at different concentrations was mixed with a protein-fluorescent material conjugate and applied to the test strip, followed by analysis by the laser-induced fluorescence detecting apparatus. The results are shown in Table 5 below, in which the differences between the strips are given as error ranges of the analyzed values. Although the error range of each strip was not out of the acceptable error range, when the reference line was located in front of the test line, or in front of the test line and at the rear of the test line, accuracy and reproducibility were preferably higher.

Accordingly, it was concluded that for reliable and reproducible results, the reference line should be located in front of the test line or both in front and at the rear of the test line, though the results in any position was not out of the acceptable error range.

TABLE 5

|  | 40 pg/ml | 400 pg/ml | 4 ng/ml |
| --- | --- | --- | --- |
| Front | 40.2 ± 4 | 403.6 ± 12 | 4.01 ± 0.2 |
| Rear | 41.3 ± 6 | 405.2 ± 35 | 4.09 ± 0.4 |
| Front and rear | 40.2 ± 3 | 403.6 ± 11 | 4.01 ± 0.1 |

EXAMPLE 16

Dispensation of Avidin Protein on NC (Nitrocellulose) Membrane

Avidin to be immobilized was diluted in PBS buffer solution to 1 or 2 mg/ml. The solution was dispensed in an amount of 0.88 μl/cm as a line with a width of 0.8 mm on the NC membrane using the Bio Dot dispenser and fixed at RH 35 to 50% for 2 hours. Then, the membrane was treated with a stabilizing solution (1% BSA, 0.05% Tween 20, 0.1% PVA) for stabilization of proteins and prevention of non-specific reactions between reagents, and equilibrated for 5 minutes (As the components of the stabilizing solution, BSA may be substituted with gelatin, Tween 20 may be substituted with Triton X-100, sucrose may be substituted with trehalose, PVA (polyvinylalcohol) may be substituted with PEG or PVP (polyvinylpyrrolidone)). After removing excess solution, the treated membrane was dried at 40° C. for 30 minutes. The resulting dry membrane was assembled with the sample pad, absorption pad, etc. and cut to a width of 4 mm using a cutter so that the final strip had a dimension of 4×60 mm.

EXAMPLE 17

Quantification of Analyte Using Avidin-Biotin (Single Test Line)

The avidin (1 mg/ml) and rabbit IgG (1 mg/ml) were dispensed in the test line region and reference line in an amount of 0.88 μl/cm over the NC membrane. The resulting membrane was stored at RH of 35 to 50% for 2 hours for immobilization. Then, the membrane was treated with a stabilizing solution (1% BSA, 0.05% Tween 20, 0.1% PVA) for stabilization of proteins and prevention of non-specific reactions between reagents, and equilibrated for 5 minutes. After removing excess solution, the treated membrane was dried at 40° C. for 30 minutes. The material to react with the protein to be analyzed via antigen-antibody reaction was fluorescently-labeled with Alexa 647. The protein to capture the analyte was coupled with biotin. Also, the antibody to bind to the protein dispensed on the reference line via antigen-antibody reaction was fluorescently-labeled with Alexa 647. The protein-fluorescent material conjugate and the protein-biotin conjugate were diluted 1/100 in a dilution buffer solution (PBS, 0.1% gelatin, 0.1% Tween 20, pH 7.4).

The prepared NC membrane, sample pad and absorption pad were adhered to the backing, cut to a dimension of 4×60 mm and assembled in a plastic housing. The PSA standard solution was diluted in a dilution buffer solution (PBST, 10 mM phosphate, 150 mM NaCl, 0.3% Tween 20, pH 7.4) to 0, 4, 8, 20 and 40 ng/ml. The concentrations of the prepared standard solutions were confirmed using a PSA ELISA kit. Each of the prepared PSA standard solutions, protein-Alexa 647 conjugate and capture protein-biotin, and the protein-Alexa 647 capable of recognizing the protein dispensed on the reference line, were dropped in a specimen input hole of the assay kit and 10 minutes later, the kit was placed in the laser-induced epifluorescence detecting apparatus according to the present invention. The apparatus was designed to display the fluorescence intensity of the detector/analyte/capture conjugate accumulated on the test line and fluorescence intensity of protein-fluorescent material conjugate on the reference line as peaks on a monitor. Also, the apparatus displayed the numerical value of fluorescence intensity of the analyte which was calculated by inputting a ratio of the fluorescence intensities of the test line and the reference line into an analogized equation by the polynomial regression method, to obtain the numerical value of the fluorescence intensity of the analyte. The results are shown in FIG. 17. The line A represents the result of the quantitative assay using avidin-biotin and the line B represents the result of the quantitative assay according to the conventional method without using avidin-biotin as a control. From the results of FIG. 17, it is noted that greater sensitivity and reproducibility can be obtained by using avidin-biotin.

EXAMPLE 17

A protein chip was prepared using polystyrene as a substrate. Each of the proteins prepared in Example 1 was mixed with 50 mM sodium bicarbonate (pH 9.6), 20 mM Tris-Cl (pH 8.5), 10 mM PBS (pH 7.2). The mixture was dispensed on the substrate, followed by immobilization at room temperature for 2 hours. After completion of the reaction, the substrate was washed twice with distilled water and a blocking buffer solution (PBS containing 0.1% BSA, 0.05% Tween 20) was added to the substrate, followed leaving at room temperature for 10 minutes, to obtain a protein chip.

Figure 22:
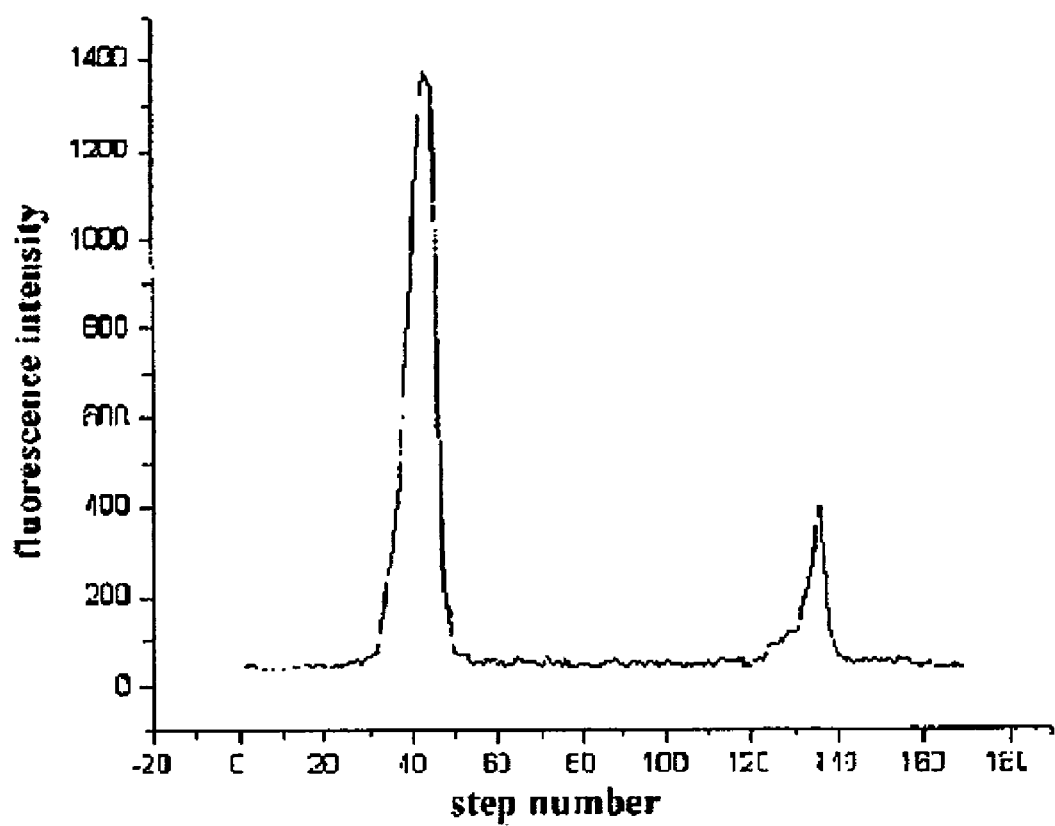
FIG. 22 is a graph showing results of quantification of a protein chip where antibody proteins are arranged in one dimension using a laser-induced epifluorescence detecting apparatus with an elliptical reflecting mirror according to the present invention.

Using the laser-induced epifluorescence detecting apparatus according to the present invention, constructed as shown in FIG. 2, the fluorescences emitted by the protein where the antibody proteins prepared as above were arranged in one dimension were measured. The results are shown in FIG. 22.

INDUSTRIAL APPLICABILITY

As described above, the lateral flow assay strip according to the present invention makes it possible to measure analyte(s) at the same time, with high sensitivity. In addition, a laser-induced epifluorescence detector of the present invention provides a collection efficiency of at least 80% fluorescence and thus makes it possible to measure multiple analytes by minimum detection limit of pg/ml.

What is claimed is:

1. A method for detecting laser-induced epifluorescence, comprising:

fixing a sample whose surface is labeled with fluorescent material at a first focal point of an elliptical or spherical reflecting mirror;

passing light emitted from a laser through an exciter filter and then through a hole of the elliptical or spherical reflecting mirror that is disposed between the exciter filter and the sample control means and focusing the filtered light to a surface of the sample positioned at the first focal point of the elliptical or spherical reflecting mirror with a proper size;

focusing scattered incident light and fluorescence emitted from the sample positioned at the first focal point of the elliptical or spherical reflecting mirror to a second focal point of the elliptical or spherical reflecting mirror by reflection of the reflecting mirror;

removing noise from the scattered incident light and the fluorescence reflected by the elliptical or spherical reflecting mirror through a spatial filter positioned at the second focal point;

converting the noise-removed light into parallel light by a collimator;

filtering the parallel light through a fluorescent filter to remove the scattered incident light; and providing a pure fluorescence component to an optical detector.

* * * * *

UNITED STATES PATENT AND TRADEMARK OFFICE
CERTIFICATE OF CORRECTION

PATENT NO. : 7,633,620 B2
APPLICATION NO. : 12/327942
DATED : December 15, 2009
INVENTOR(S) : Kie-Bong Nahm et al.

It is certified that error appears in the above-identified patent and that said Letters Patent is hereby corrected as shown below:

Col. 9, line 51, replace "F1α" with --F1a--

Col. 11, line 14, replace "aline" with --saline--

Col. 13, line 29, replace "106" with --$10^6$--

Col. 15, line 37, replace "104" with --$10^{-4}$--

Col. 36, line 64, replace "11200" with --1/200--

Signed and Sealed this
Third Day of May, 2011

David J. Kappos
*Director of the United States Patent and Trademark Office*